United States Patent
Greenwald et al.

(10) Patent No.: US 6,824,766 B2
(45) Date of Patent: Nov. 30, 2004

(54) BIODEGRADABLE HIGH MOLECULAR WEIGHT POLYMERIC LINKERS AND THEIR CONJUGATES

(75) Inventors: Richard B. Greenwald, Somerset, NJ (US); Hong Zhao, Edison, NJ (US)

(73) Assignee: Enzon, Inc., Piscataway, NJ (US)

( * ) Notice: Subject to any disclaimer, the term of this patent is extended or adjusted under 35 U.S.C. 154(b) by 377 days.

(21) Appl. No.: 09/888,072

(22) Filed: Jun. 22, 2001

(65) Prior Publication Data

US 2002/0009426 A1 Jan. 24, 2002

Related U.S. Application Data

(63) Continuation-in-part of application No. 09/293,557, filed on Apr. 15, 1999, now Pat. No. 6,251,382.
(60) Provisional application No. 60/082,105, filed on Apr. 17, 1998.

(51) Int. Cl.[7] .................................. A61K 31/785
(52) U.S. Cl. ................ 424/78.18; 514/248; 514/283; 546/47; 546/70; 525/54.1; 525/54.2; 530/323
(58) Field of Search .................. 514/283, 279; 424/78.18; 525/54.1; 530/322

(56) References Cited

U.S. PATENT DOCUMENTS 5,965,566 A * 10/1999 Greenwald et al. ......... 514/279
6,011,042 A * 1/2000 Greenwald et al. ......... 514/283

OTHER PUBLICATIONS

Greenwald, RB, Pendri, A, Conover C, Gilbert C, Yang R, Xia J. "Drug delivery systems. 2. Camptothecin 20–O–poly-(ethylene glycol) ester transport forms." J Med Chem. May 10, 1996; 39(10):1938–1940.*

* cited by examiner

Primary Examiner—Jon P. Weber
Assistant Examiner—Anand Desai
(74) Attorney, Agent, or Firm—Muserlian, Lucas and Mercanti

(57) ABSTRACT

The present invention includes polymeric transport systems corresponding to the formula:

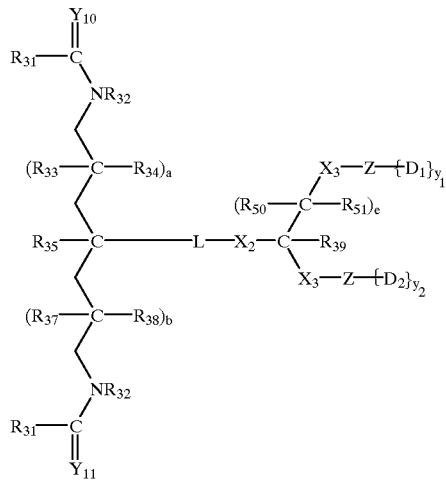

(X)

wherein:

$R_{31}$ is a linear or branched polymer residue; $Y_{10}$ and $Y_{11}$ are independently O, S, or $NR_{40}$; $X_2$ is O, S or $NR_{41}$; $R_{32\text{-}35}$, $R_{37\text{-}41}$, $R_{50}$ and $R_{51}$ are independently selected among hydrogen, $C_{1\text{-}6}$ alkyls, $C_{3\text{-}12}$ branched alkyls, $C_{3\text{-}8}$ cycloalkyls, $C_{1\text{-}6}$ substituted alkyls, $C_{3\text{-}8}$ substituted cycloalkyls, aryls, substituted aryls, aralkyls, $C_{1\text{-}6}$ heteroalkyls and substituted $C_{1\text{-}6}$ heteroalkyls; a, b and e are each independently selected positive integers; L is an amino acid residue or a bifunctional linker; $X_3$ is

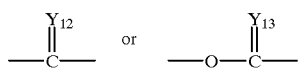

wherein $Y_{12}$ and $Y_{13}$ are independently O, S, or $NR_{41}$; Z is a bond, a moiety that is actively transported into a target cell, a hydrophobic moiety or combinations thereof; $D_1$ and $D_2$ are OH, a residue of a hydroxyl, a residue of an amine-containing moiety or a leaving group; and $y_1$ and $y_2$ are independently selected positive integers.

15 Claims, 19 Drawing Sheets

US 6,824,766 B2

BIODEGRADABLE HIGH MOLECULAR WEIGHT POLYMERIC LINKERS AND THEIR CONJUGATES

CROSS-REFERENCE TO RELATED APPLICATION

This application is a continuation-in-part of U.S. patent application Ser. No. 09/293,557 filed Apr. 15, 1999, now U.S. Pat. No. 6,251,382 which claims the benefit of priority from U.S. Patent Provisional Application Serial No. 60/082,105 filed Apr. 17, 1998, the contents of each of which are incorporated herein by reference.

TECHNICAL FIELD

The present invention relates to new types of biodegradable, terminally activated polymers which are useful in forming conjugates of bioactive materials. In particular, the invention relates to biodegradable, polymeric-based conjugates having increased therapeutic payloads and methods of preparing the same.

BACKGROUND OF THE INVENTION

Over the years, several methods of administering biological y-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Science*, 16th Ed, A. Osol, Ed. (1980), the disclosure of which is incorporated by reference herein.

Prodrugs are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs.

Incorporating a polymer as part of a prodrug system has been suggested to increase the circulating life of a drug. However, it has been determined that when only one or two polymers of less than about 10,000 daltons each are conjugated to certain biologically active substances such as alkaloid compounds, the resulting conjugates are rapidly eliminated in vivo, especially if a somewhat hydrolysis-resistant linkage is used. In fact, such conjugates are so rapidly cleared from the body that even if a hydrolysis-prone ester linkage is used, not enough of the parent molecule is regenerated in vivo to be therapeutic.

As an outgrowth of the work in the prodrug field, it has been thought that it would be beneficial in some situations to increase the payload of the polymeric transport form. This technique was offered as an alternative to the many approaches in which a single molecule of a therapeutic moiety containing a substitutable hydroxyl moiety is attached to a terminal group found on the polymer. For example, commonly-assigned PCT publication WO96/23794 describes bis-conjugates in which one equivalent of the hydroxyl-containing drug is attached to each terminal of the polymer. In spite of this advance, techniques which would further increase the payload of the polymer have been sought. In addition, technologies for forming prodrugs of therapeutic moieties having a substitutable amino group have also been sought. The present invention addresses these needs.

SUMMARY OF THE INVENTION

The present invention includes compounds of formulae (X) and (XI):

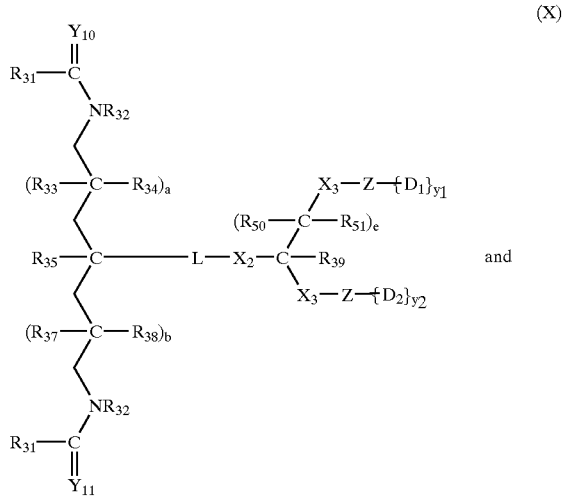

(X)

and

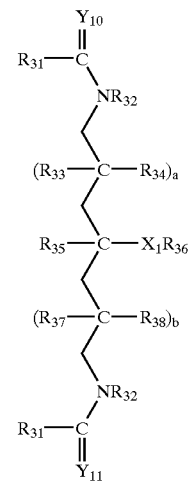

(XI)

wherein:

$R_{31}$ is a linear or branched polymer residue;

$Y_{10}$ and $Y_{11}$ are independently O, S, or $NR_{40}$;

$R_{32}$–$R_{40}$, $R_{50}$ and $R_{51}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

a, b and e are each independently selected positive integers, preferably from about 1 to about 6;

$X_1$ and $X_2$ are independently O, S or $NR_{41}$;
wherein $R_{41}$ is selected from the same group as that which defines $R_{40}$;
L is an amino acid residue or a bifunctional linker.
$X_3$ is

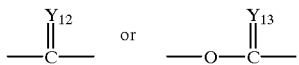

wherein $Y_{12}$ and $Y_{13}$ are independently O, S, or $NR_{40}$;
Z is selected from the group consisting of a bond, a moiety that is actively transported into a target cell, a hydrophobic moiety, and combinations thereof;
$D_1$ and $D_2$ are independently one of OH a residue of a hydroxyl-containing moiety, a residue of an amine-containing moiety or a leaving group; and
$y_1$ and $y_2$ are each independently a positive integer.
In preferred aspects of the above embodiment,
$R_{31}$ preferably a PEG residue;
$Y_{11}$ and $Y_{12}$ are both O;
$R_{22}$–$R_{40}$, $R_{50}$, and $R_{51}$ are each hydrogen or a $C_{1-4}$ alkyl;
a and b hare each 1;
$y_1$ and $y_2$ are both one; and
$D_1$ and $D_2$ are both residues of either a hydroxyl- or amine-containing moiety such as one having biological activity as defined herein.
With regard to L in formulae (X) and (XI), a non-limiting list of suitable amino acid residues include those of the formula:

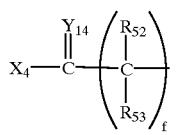

wherein $X_4$ is O, S or $NR_{42}$, $Y_{14}$ is O, S, or $NR_{45}$; where $R_{42}$, $R_{45}$ and $R_{52}$–$R_{53}$ are selected from the same group which defines $R_{40}$; and (f) is a positive integer, preferably from about 1 to about 2. Alternatively, a non-limiting list of suitable bifunctional linkers include:

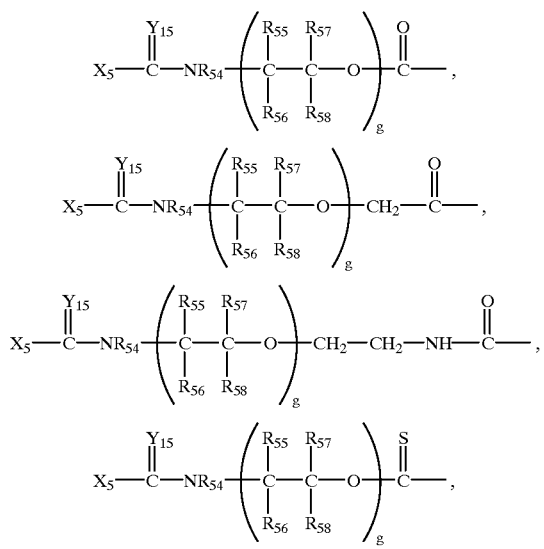

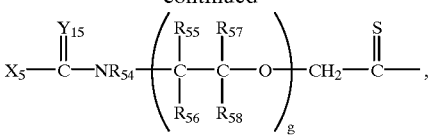

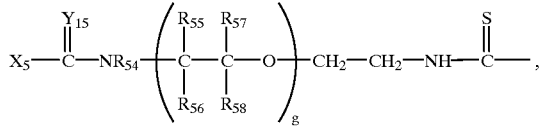

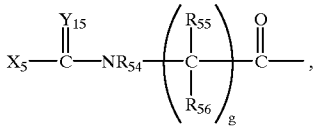

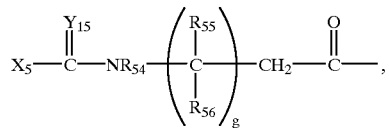

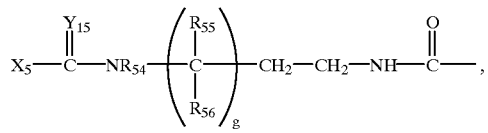

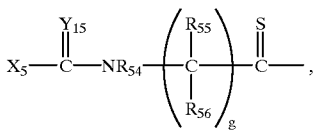

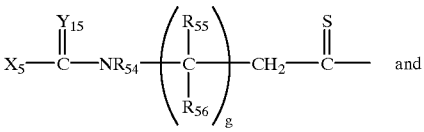

and

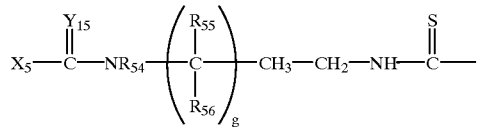

wherein $X_5$ is O, S or $NR_{43}$;
$Y_{15}$ is O, S, or $NR_{44}$;
$R_{43}$, $R_{44}$ and $R_{54}$–$R_{58}$ are selected from the same group which defines $R_{40}$; and g is a positive integer, preferably from about 1 to about 2.
With regard to (Z), it will be understood that in addition to being a covalent bond, Z is covalently linked to $[D]_y$, so that Z is a moiety that is actively transported into a target cell, a hydrophobic moiety or a combination thereof. Optionally, Z is monovalent, multivalent, or more preferably, bivalent, wherein (y) is 1 or 2. Z itself optionally includes an amino acid residue, a sugar residue, a fatty acid residue, a peptide residue, a $C_{1-18}$ alkyl, a substituted aryl, a heteroaryl, —C(=O), —C(=S), and —C(=$NR_{42}$), where $R_{42}$ is selected from the same group which defines $R_{40}$.
When Z includes at least one amino acid residue, the amino acid is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When Z includes a peptide, the peptide ranges in size, for instance, from about 2 to about 10 amino acid residues. In one preferred embodiment, the peptide is Gly-Phe-Leu-Gly or Gly-Phe-Leu.

Methods of preparing and using the same are also disclosed.

In more general aspects, the invention includes compounds of the formula:

$$(D)_n\text{-M-}(R_1)_m \qquad (I)$$

wherein
(m) and (n) are independently selected positive integers, preferably from about 1 to about 6 each;
D is a residue of a biologically active moiety;
M is a multifunctional linker/spacer moiety; and
$R_1$ is a polymer residue.

With respect to the linking of the polymer strands, the artisan is provided with higher total molecular weight polymers which are useful in providing therapeutic conjugates with relatively long $T_{1/2}$'s. There are several advantages associated with these types of polymers. For example, depending upon the linkages used to attach the polymer strands to the multifunctional spacer groups, the artisan can design relatively high molecular weight polymeric transport systems which will predictably biodegrade into polymers of relatively low molecular weight which are more readily eliminated from the body than the singular polymer of higher molecular weight. Secondly, because relatively small molecular weight polymers are used to build the biodegradable transport form, the polydispersity associated with some single strand high molecular polymers such as when PEG has a molecular weight of over 40 kDa is substantially avoided.

Additional advantages associated with using the multifunctional spacers in the polymers of the present invention are that there is a large number of multifunctional moieties readily available. Thus, the artisan can prepare polymeric prodrug systems having high degrees of loading, i.e. 3–6 or more molecules of active drug per transport system. A still further advantage of the multifunctional spacers of polymeric systems of the present invention is that the artisan can form prodrugs of almost any therapeutic molecule. For example, the multifunctional spacer can be designed to include the capability of accommodating a linker for attaching to hydroxyl residues, amine residues, sulfhydral residues, etc. found on organic molecules, proteins, peptides, enzymes, etc. Another advantage is that the linkers can be selected to achieve a proper balance between the rate of parent drug-polymer linkage hydrolysis on the one hand and the rate of clearance of prodrug from the body on the other which is caused by lower molecular weight polymer portions being released from the transport system. The linkages between the polymer and the parent compounds, also referred to herein as biologically-active nucleophiles, hydrolyze at a rate which allows a sufficient amount of the parent molecules to be released in vivo before clearance of the prodrug from the plasma or body.

The high payload polymeric conjugates of the present invention are thus unique delivery systems which can contain up to several molecules of a drug per unit.

In the case of compounds corresponding to formula (X), the artisan is provided with a unique polymer transport form which can deliver more than one equivalent of biologically active material using a backbone which includes multiple strands of polymer. In the case of compounds corresponding to Formula (XI), the artisan is provided a useful intermediate which can be functionalized to include any number of bifunctional spacers and multifunctional terminal groups which allow the attachment of one, two or more equivalents of biologically active material or leaving groups for later reaction and coupling with biologically active materials, e.g. drugs, small molecules, proteins, peptides, etc.

DETAILED DESCRIPTION OF THE INVENTION

Figure 1:
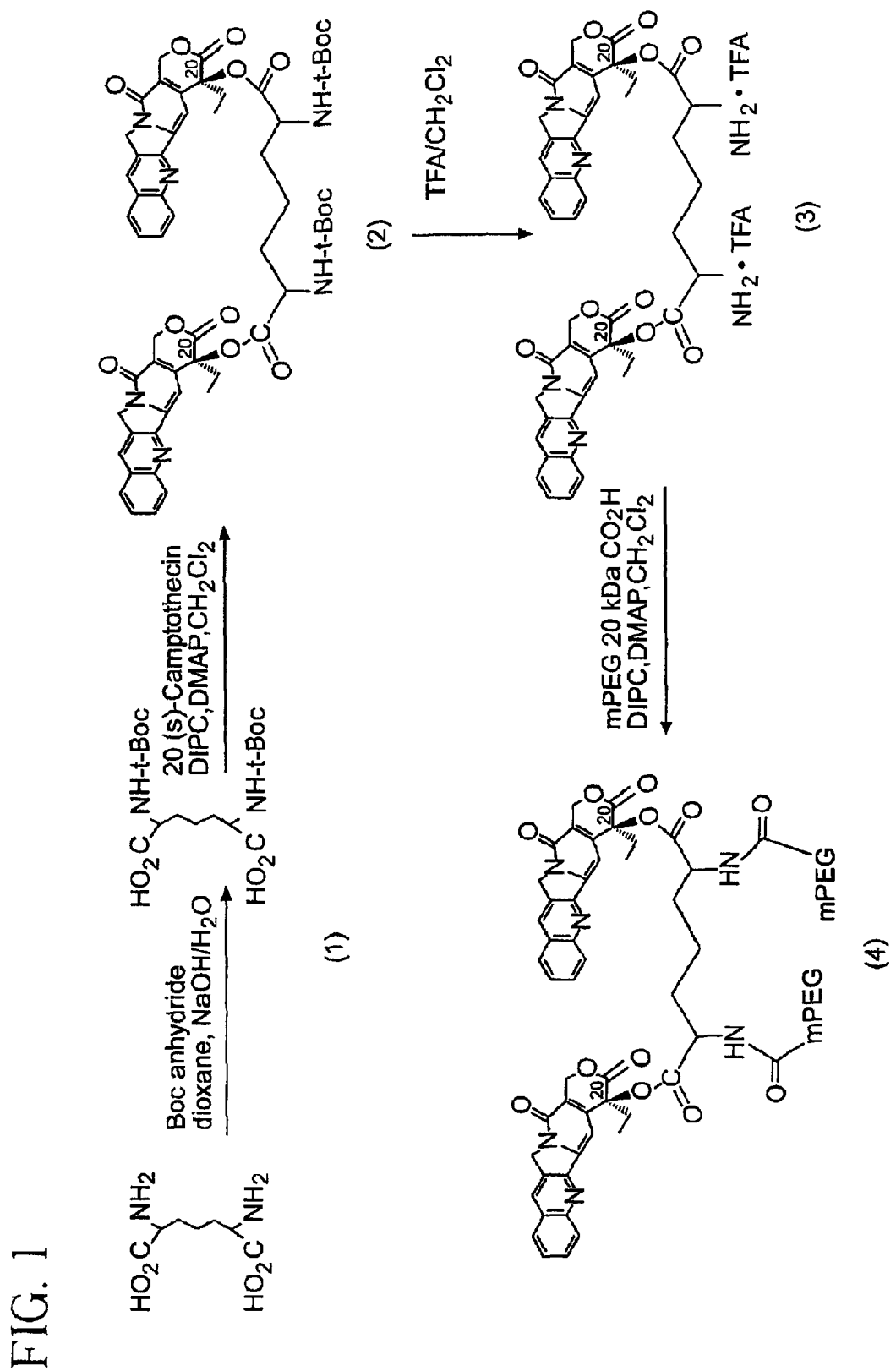
FIGS. 1–11, 12*a–c* and 13–17 provide reaction schemes for preparing compounds described in the present application.

One aspect of the invention includes providing prodrug polymer compositions which include two or more polymer strands, each having the same or a different molecular weight, linked together by a multifunctional linker/spacer component which also serves as the attachment point for one or more biologically active moieties. For example, molecules of the drug can be individually attached via ester linkage to separate points on the multifunctional moiety and the individual polymer strands are attached to the multifunctional moiety via a carbamate or other type of covalent linkage, such as but not limited to ester, carbonate, amide, urea, etc. between the multifunctional moiety and the drug molecule and/or the polymer residues.

As can be seen from the Figures, the inventive drug transport forms include multifunctional moieties, e.g. di-, tri-, tetra-, penta-, hexa-, octa-, etc., which are linked to drug molecules and polymer strands.

For purposes of Illustration, a general formula (I) is provided:

$$(D\text{-})_n\text{-M-}(R)_m \qquad (I)$$

wherein:
(m) and (n) are positive integers, preferably from about 1 to about 6 each;
D is a residue of a biologically active moiety;
M is a multifunctional linker/spacer moiety; and
$R_1$ is a polymer residue.

For example, if (m) and (n) are each 2, M, of course, would be a tetrafunctional moiety such as an aminopimelic acid residue. If (m) is 2 and (n) is 3, M would be a pentafunctional moiety. Preferably, (m) is 2 and (n) is 4. Examples of suitable reagents which can be used to impart the multifunctional moiety to the final compositions of the present invention include aspartic acid and diaminopimelic acid. Polyfunctional amino acids, if desired, can also be used.

It will be understood that within the scope of the present invention are prodrugs which include a mixture of linkages attaching various drug molecules and/or different multifunctional spacer moieties. For example, one molecule of the drug can be attached via an ester linkage to the multifunctional moiety and a second drug molecule can be attached via a carbamate linkage. The polymers can be similarly linked together or to the multifunctional moiety, e.g. one polymer is linked via an ester and another polymer has a carbamate linkage to the multifunctional spacer moiety.

In other aspects of the invention, methods of preparing the compositions described herein and methods of treatment using the compositions are provided.

For purposes of the present invention, the term "residue" shall be understood to mean that portion of a biologically active compound or polymer which remains after it has undergone a substitution reaction as described herein.

For purposes of the present invention, the term "alkyl" shall be understood to include straight, branched, substituted $C_{1-12}$ alkyls, including alkoxy, $C_{3-8}$ cycloalkyls or substituted cycloalkyls, etc.

The term "sufficient amounts" for purposes of the present invention shall mean an amount which achieves a therapeutic effect as such effect is understood by those of ordinary skill in the art.

A non-limiting list of some of the preferred compounds corresponding to Formula (I) are set forth below. In each sub-formula, the variables used have the following definitions:

D is a residue of a biologically active moiety;

$R_1$ and $R_1'$ are independently selected polymer residues;

all other groups, i.e. $R_2$, $R_3$, . . . $R_n$ are independently selected from among hygrogen, $C_{3-6}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

p is a positive integer, preferably ranging from about 1 to about 12;

k, m, n and every other lower case alphabet letter is zero (0) or a positive integer, preferably ranging from about 1 to about 12; and all Y groups, i.e. $Y_{1-4}$ and $Y_{1-4}'$ are independently one of O, S and $NR_2$.

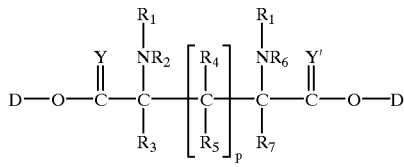

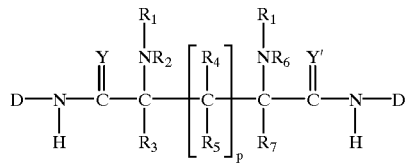

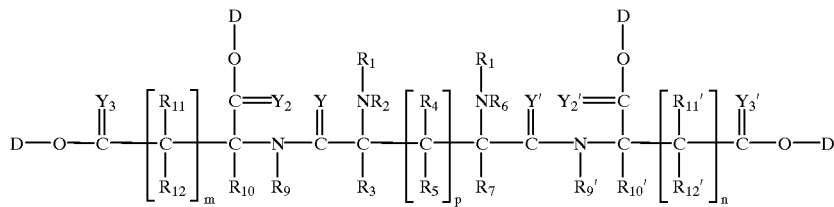

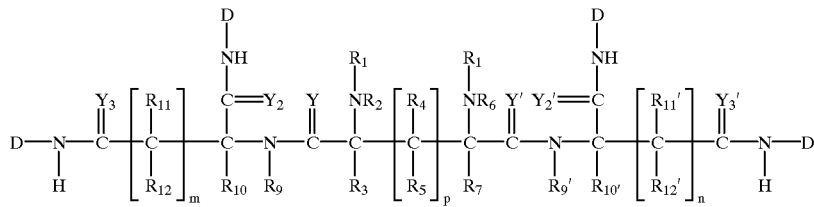

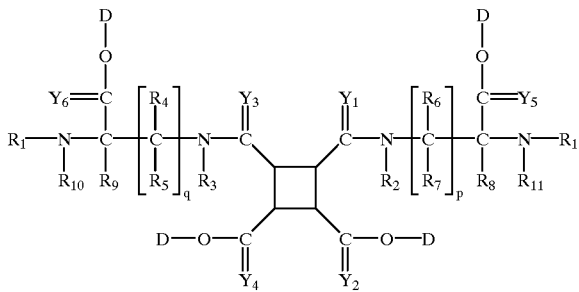

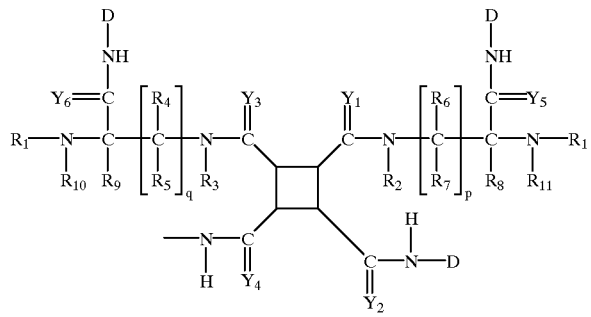

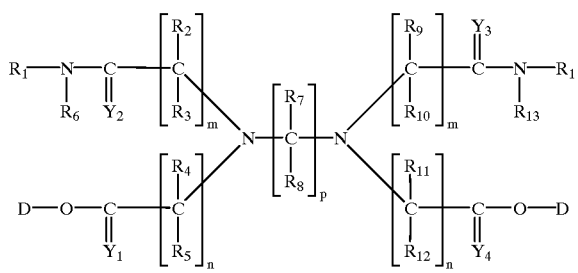

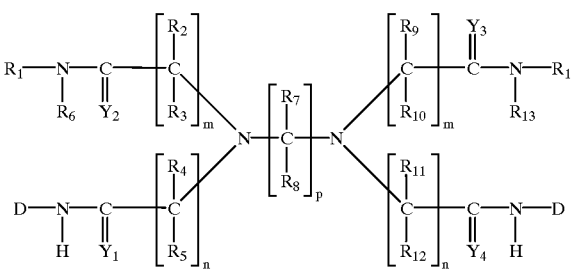

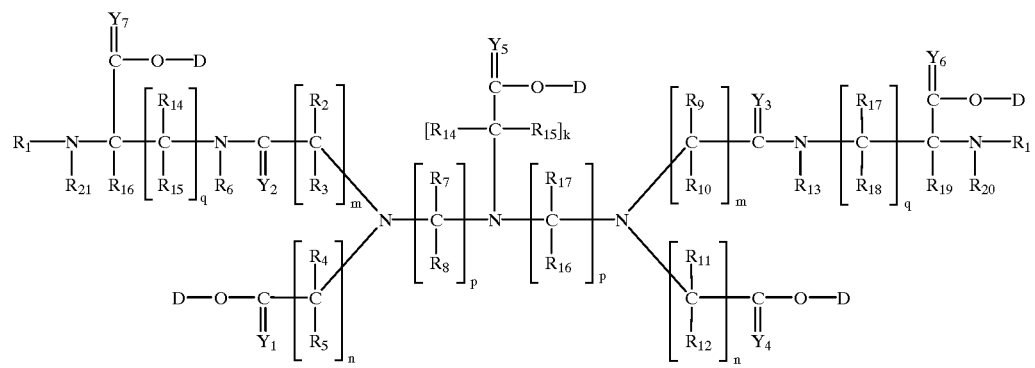
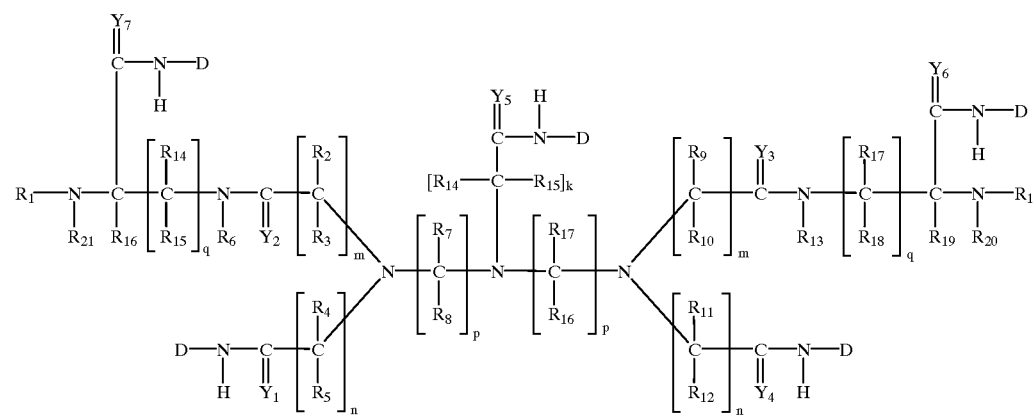
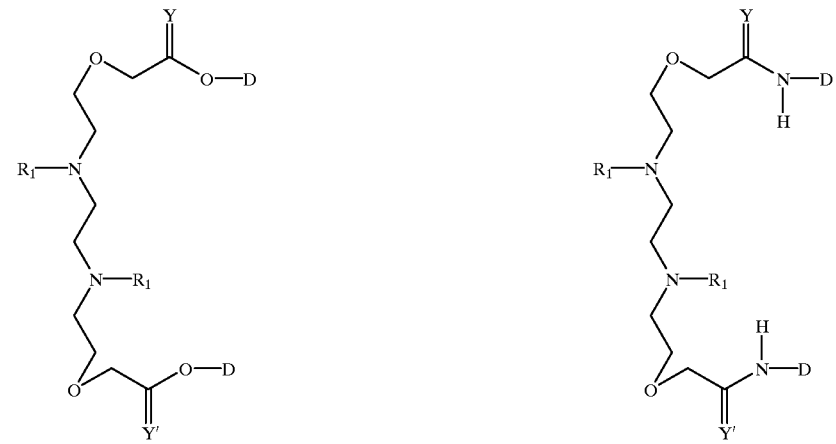
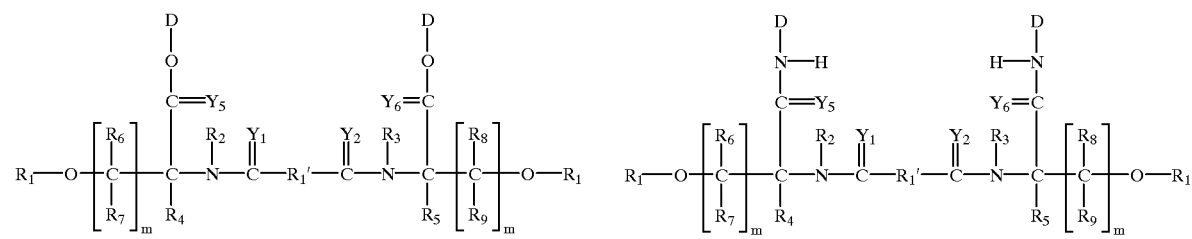

-continued
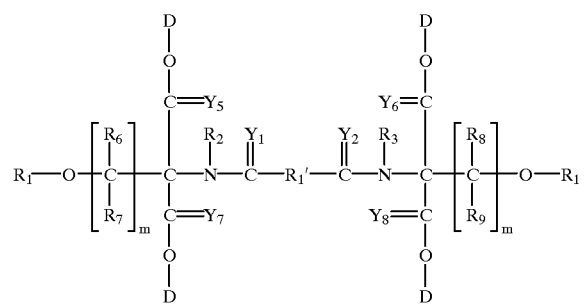
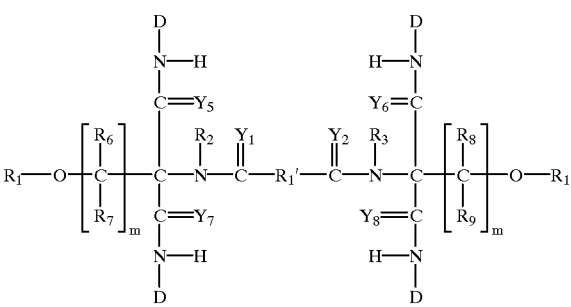
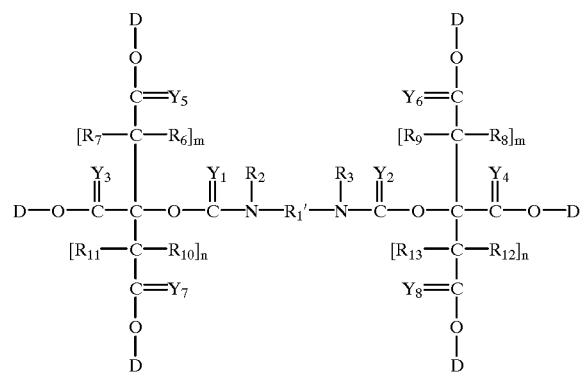
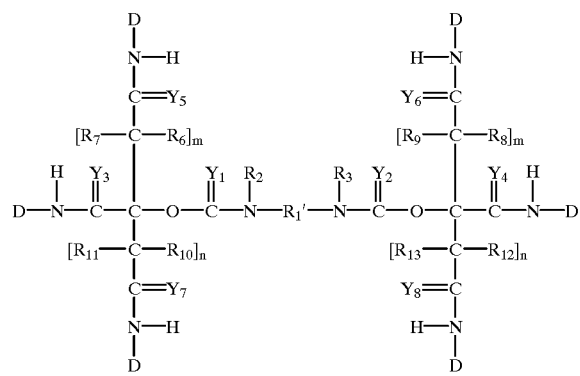
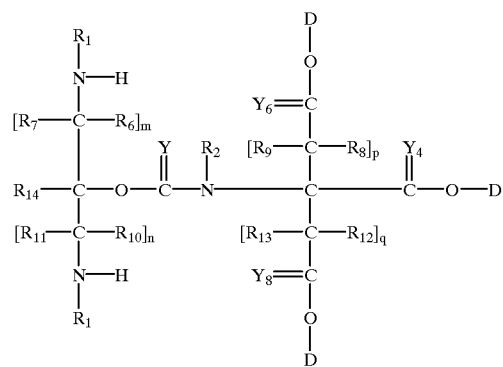
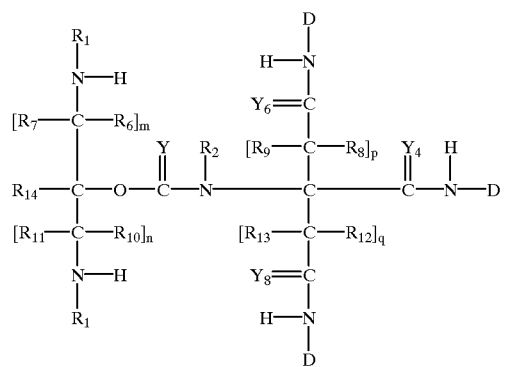
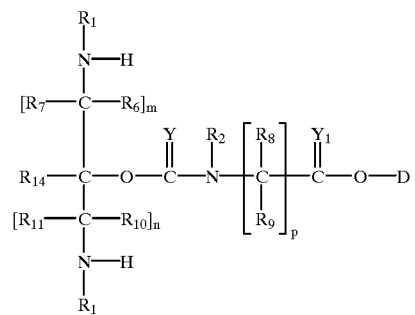
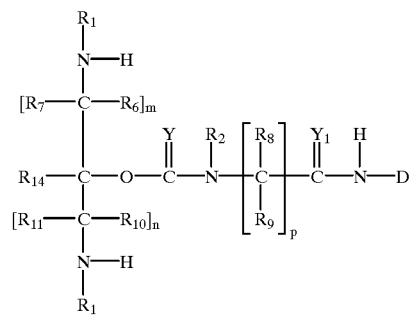

-continued
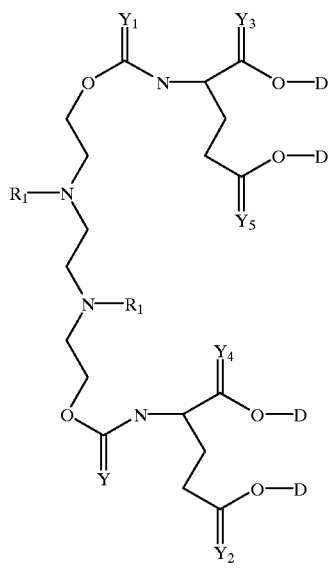
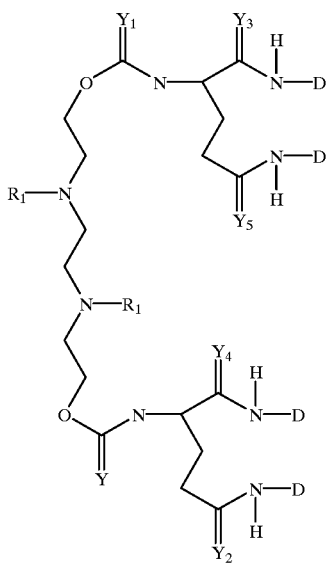
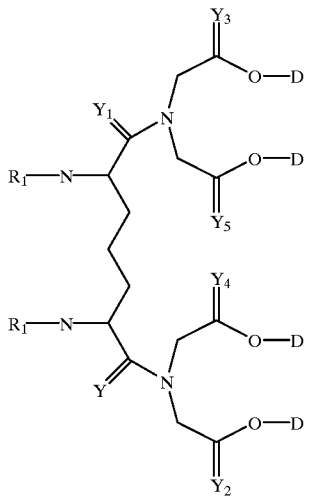
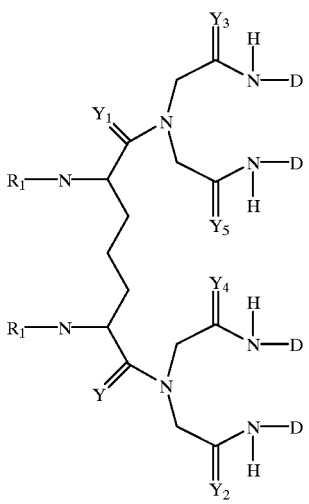
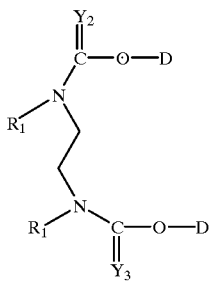
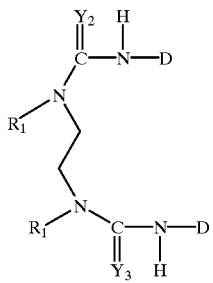
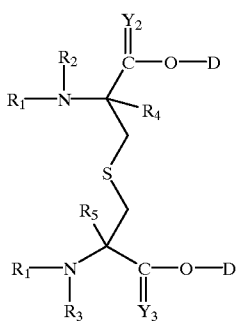
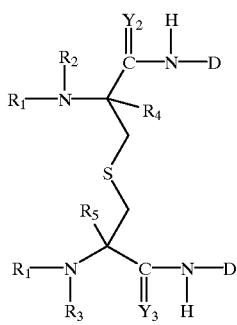

-continued

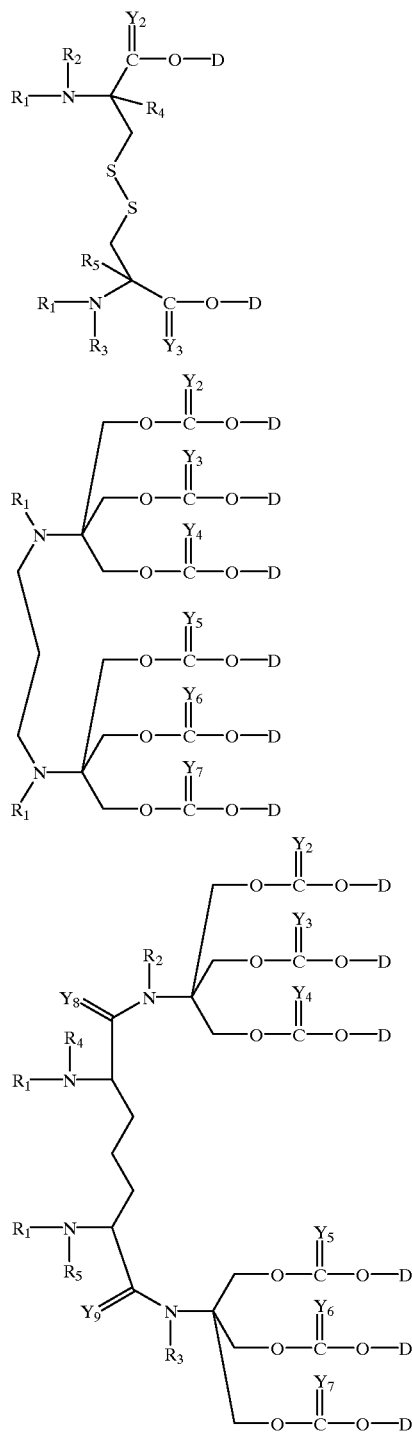
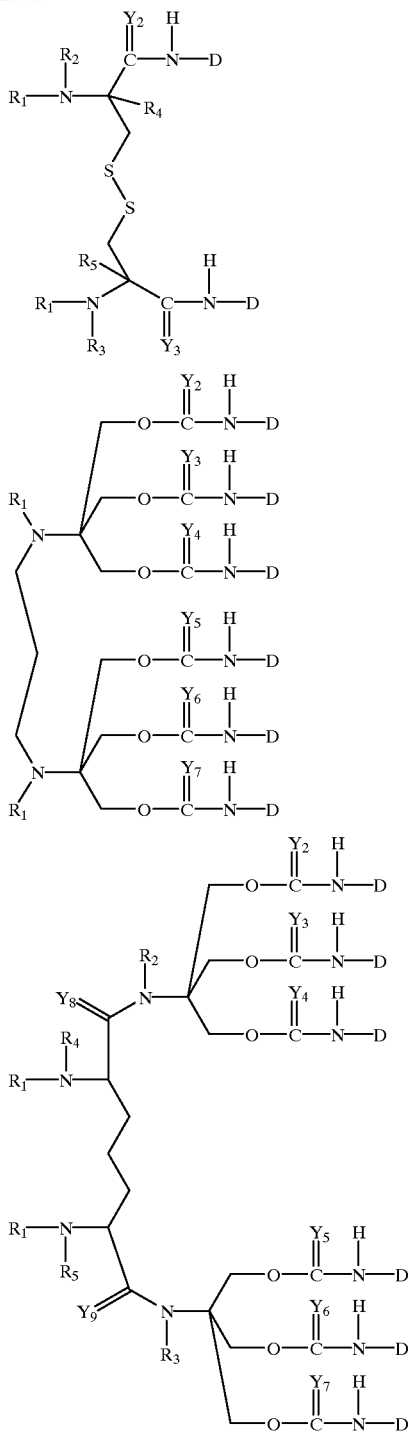

A. Multifunctional Linker/Spacer Moieties

The M moiety provides the backbone for attaching the various polymeric and biologically active moieties. Those skilled in the art will readily appreciate that generally the M moiety is derived from a group which is at least bifunctional and includes at least two sites for drug or polymer attachment.

In certain aspects of the invention, the M moiety includes one or more additional spacer groups which can be added to the M moiety as part of the synthesis using standard organic synthesis techniques. Suitable spacers are attached to proximal to the multifunctional M moiety. The spacer moiety may be a heteroalkyl, alkoxy, alkyl containing up to 18 carbon atoms or even an additional polymer chain. Examples of suitable spacers include polymers, —CO—NH—(CH$_2$—)$_d$X$_2$, —CO—NH—(CH$_2$—CH$_2$—O—)$_d$X$_2$

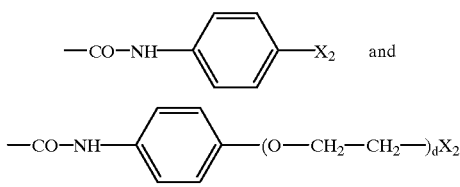

where (d) is an integer between about 1 and about 18 inclusive and ($X_2$) is X OH, $NH_2$ or COOH.

B. Substantially Non-Antigenic Polymers

As stated above, $R_1$ is a polymeric residue which is preferably substantially non-antigenic. Suitable examples of such polymers include polyalkylene oxides such as polyethylene glycols. The general formula for PEG and its derivatives is,

where (x) represents the degree of polymerization (i.e. from about 10 to about 2,300) or number of repeating units in the polymer chain and is dependent on the molecular weight of the polymer, (n3) is zero or a positive integer, (A) is a terminal or capping group such as an amino, carboxy, halo, OH, $C_{1-6}$ alkyl, preferably methyl and (A') is the same as (A) or another (A) moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated here in by reference. It will be understood that the water-soluble polymer can be functionalized for attachment to the multifunctional moiety M herein. As an example, the PEG portion of the inventive compositions can be one of the following non-limiting compounds:

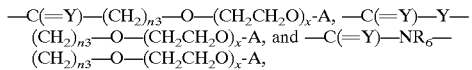

where Y is O, S or NR2 and A, $R_2$ and $R_6$, (n3) and (x) are is defined above.

In many aspects of the present invention, polyethylene glycols (PEG's), mono-activated, $C_{1-4}$ alkyl-terminated PAO's such as mono-methyl-terminated polyethylene glycols (mPEG's) are preferred.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 are usually selected for the purposes of the present invention. Molecular weights of from about 5,000 to about 50,000 are preferred and 20,000 to about 40,000 are particularly preferred. It will be appreciated that the molecular weight recitations are based upon the total amount of polymer per transport system. The number average molecular weight of the polymer selected for inclusion in the prodrug must be of a magnitude which is sufficient to allow sufficient circulation of the prodrug" before hydrolysis of the linker. Within the ranges provided above, the sum of the polymer strand molecular weight is preferably at least about 20,000 for chemotherapeutic and organic moieties. In the case of some nucleophiles such as certain proteins, enzymes and the like, the number average molecular weight of the polymeric residues ranges from about 2,000 to about 20,000.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bi-functional linking groups are also contemplated.

C. Prodrug Candidates

In a preferred aspect of this invention, the D moiety is a residue of a biologically active compound having an available hydroxyl or amino group which is capable of undergoing a substitution reaction for atatchment to the multifunctional moeity. Such compounds are suitable for medicinal or diagnostic use in the treatment of animals, e.g., mammals, including humans, for conditions for which such treatment is desired.

1. Residues of Hydroxyl-Containing Compounds a. Camptothecin and Related Topoisomerase I Inhibitors Camptothecin is a water-insoluble cytotoxic alkaloid produced by *Camptotheca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. Camptothecin and certain related analogues share the structure:

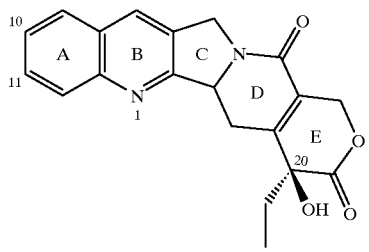

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-7}$ alkoxy, optionally linked to the ring by a heteroatom i.e. —O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re Pat. No. 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. Representative taxanes are shown below.

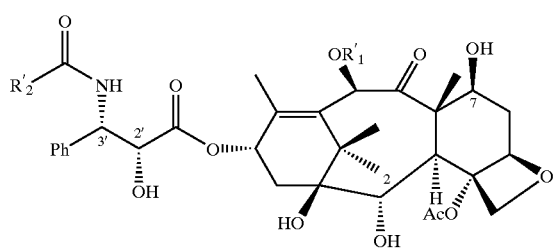

Paclitaxel: $R_{1'} = C_6H_5$; $R_{2'} = CH_3C(=O)$;
Taxotere: $R_{1'} = (CH_3)_3C(=O)$; $R_{2'} = H$ These derivatives have been found to be effective anti-cancer agents. Numerous studies indicate that the agents have activity against several malignancies. To date, their use has been severely limited by, among other things, their short supply, poor water solubility and a tendency to cause hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. The only limitation on the taxane is that it must be capable of undergoing a hydroxyl based substitution reaction such as at the 2' position. Paclitaxel, however, is a preferred taxane.

c. Additional Biologically-Active Moieties

In addition to the foregoing molecules, the prodrug formulations of the present invention can be prepared using many other compounds. For example, biologically-active compounds such as conjugates derived from compounds such as podophyllotoxin:

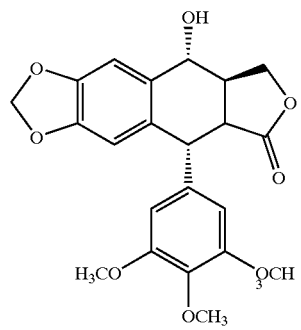

triazole-based antifungal agents such as fluconazole:

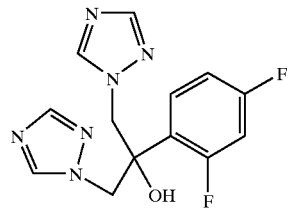

or ciclopirox:

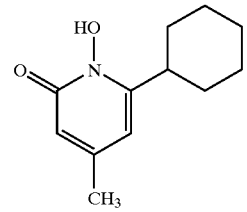

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other antitumor agents; cardiovascular agents such as forskolin; antineoplastics such as combretastatin, vinblastine, doxorubicin, maytansine, etc.; anti-infectives such as vancomycin, erythromycin, etc.; anti-fungals such as nystatin, amphoteracin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiol.* 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within in the scope of the present invention. It is also to be understood that the prodrug conjugates of the present invention may also include minor amounts of compounds containing not only one equivalent of drug and polymer but also a moiety which does not effect bioactivity in vivo. For example, it has been found that in some instances, in spite of reacting diacids with drug molecules having a single linkage point, the reaction conditions do not provide quantitative amounts of prodrugs with two equivalents of drug per polymer. By-products of the reactants can sometimes be formed such as acyl ureas if carbodiimides are used.

2. Residues of Amine-Containing Compounds

In some aspects of the invention, B is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and gemcitabine shown below:

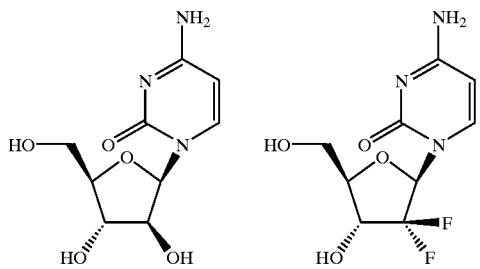

Alternatively, B can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

Suitable proteins, polypeptides, enzymes, peptides and the like having at least one available amino group for polymer attachment include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. after the prodrug transport portion has hydrolyzed.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a polypeptide demonstrating in vivo bioactivity. This includes amino acid sequences, nucleic acids (DNA, RNA) peptide nucleic acids PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

The foregoing list is meant to be illustrative and not limiting for the compounds which can be modified. Those of ordinary skill will realize that other such compounds can be similarly modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine containing position which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by the prodrug transport system described herein, may remain inactive until entering a cancer or tumor cell, whereupon it is activated by the cancer or tumor cell chemistry, e.g., by an enzyme reaction unique to that cell.

D. Synthesis of the Polymeric Prodrug Transport System

Figure 2:
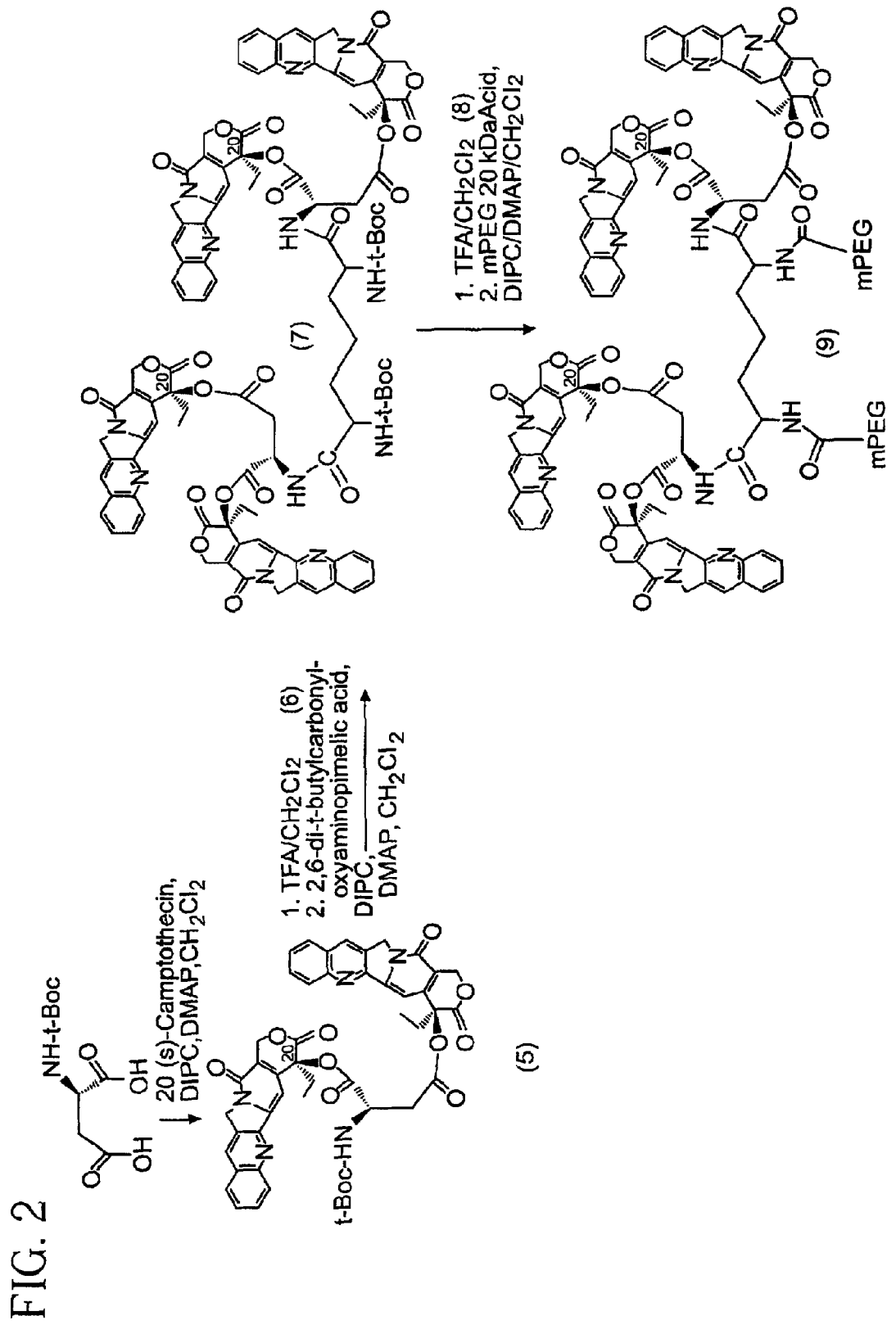
Figure 3:
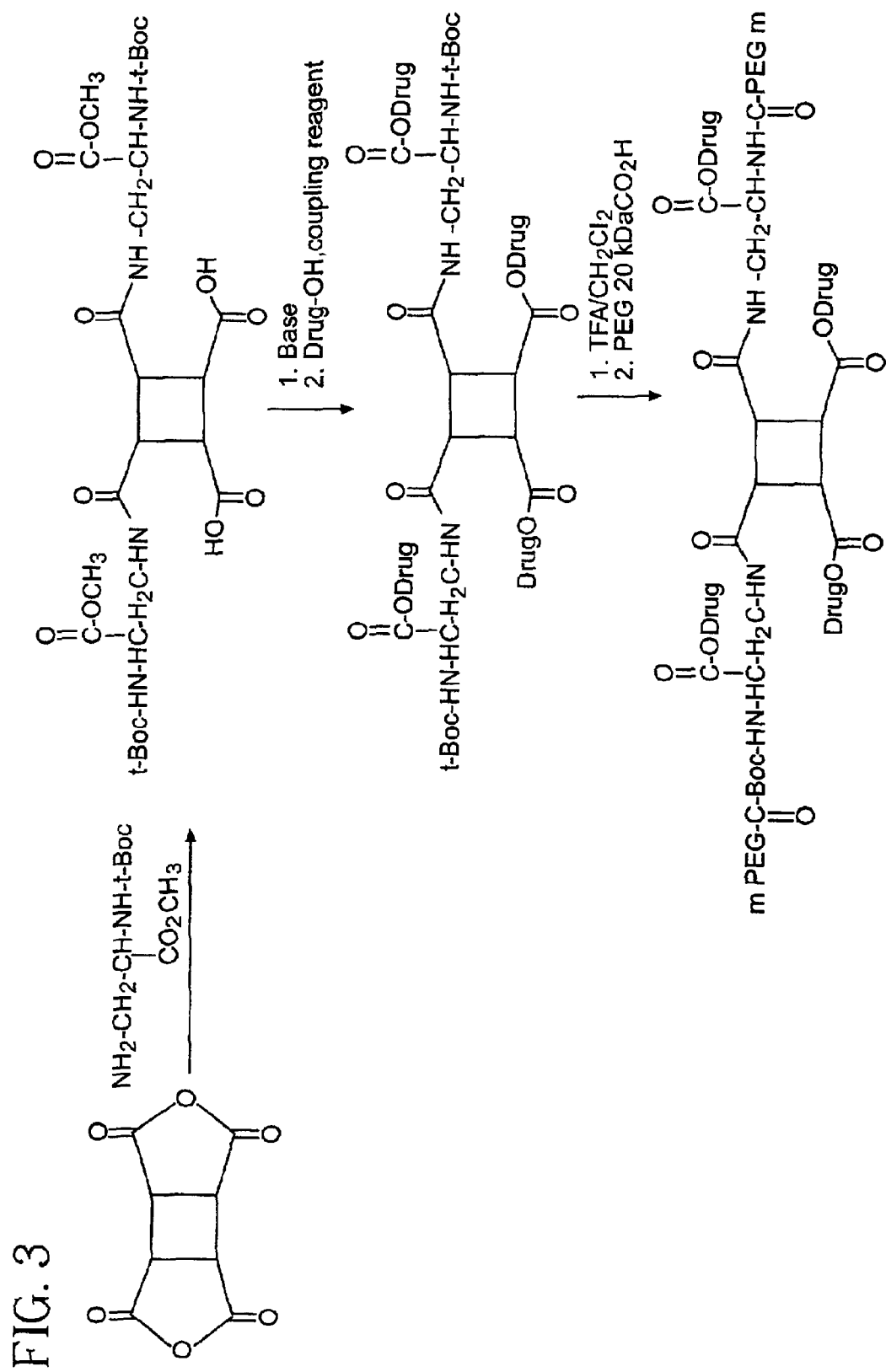

The polymeric conjugates of the present invention can be prepared in at least two general fashions. In the first method, the biologically active moiety or drug, e.g., Drug-OH or Drug-NH$_2$ is first attached to a partially blocked multifunctional moiety. Suitable protecting groups useful for this purpose may be any of a variety of organic moieties known to those of ordinary skill in the art and include, without limitation, t-Boc (tert-butyloxycarbonyl), Cbz (carbobenzyloxy) and TROC (trichloroethoxycarbonyl). Thereafter, the resultant intermediate is then deblocked with a strong acid such as trifluoroacetic acid (TFA) or other haloacetic acid, HCL, sulfuric acid, etc., or by using catalytic hydrogenation and reacted with the polymeric residue to form the final product. See also, for example, FIGS. 1–3.

Alternatively, in the second method, a multifunctional moiety is first reacted with an activated polymer such as PEG-NH$_2$. Thereafter, the resultant intermediate is reacted with the biologically active moiety or drug, e.g., Drug-OH or Drug-NH$_2$ in order to form the final compound.

Figure 4:
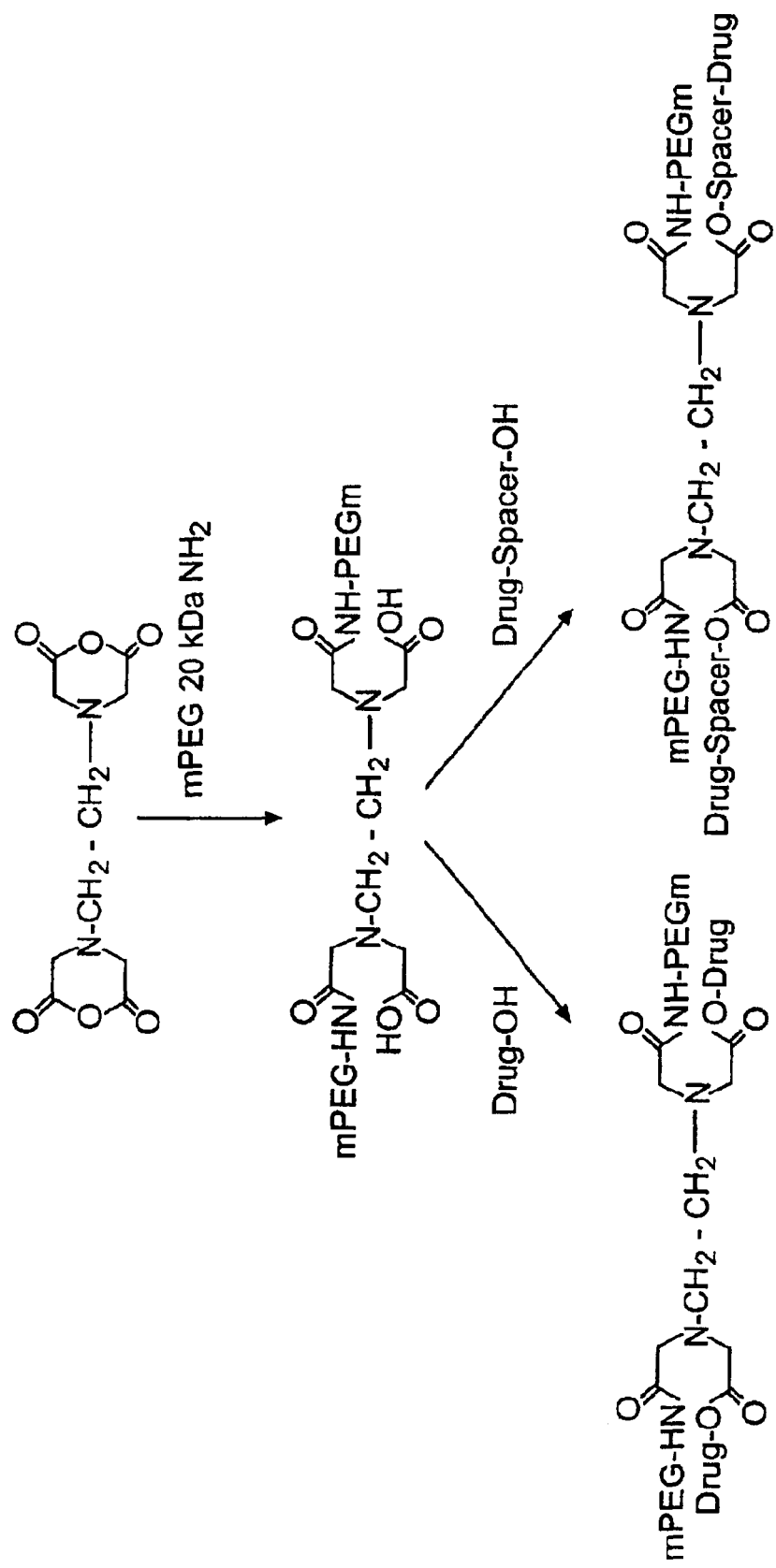
Figure 5:
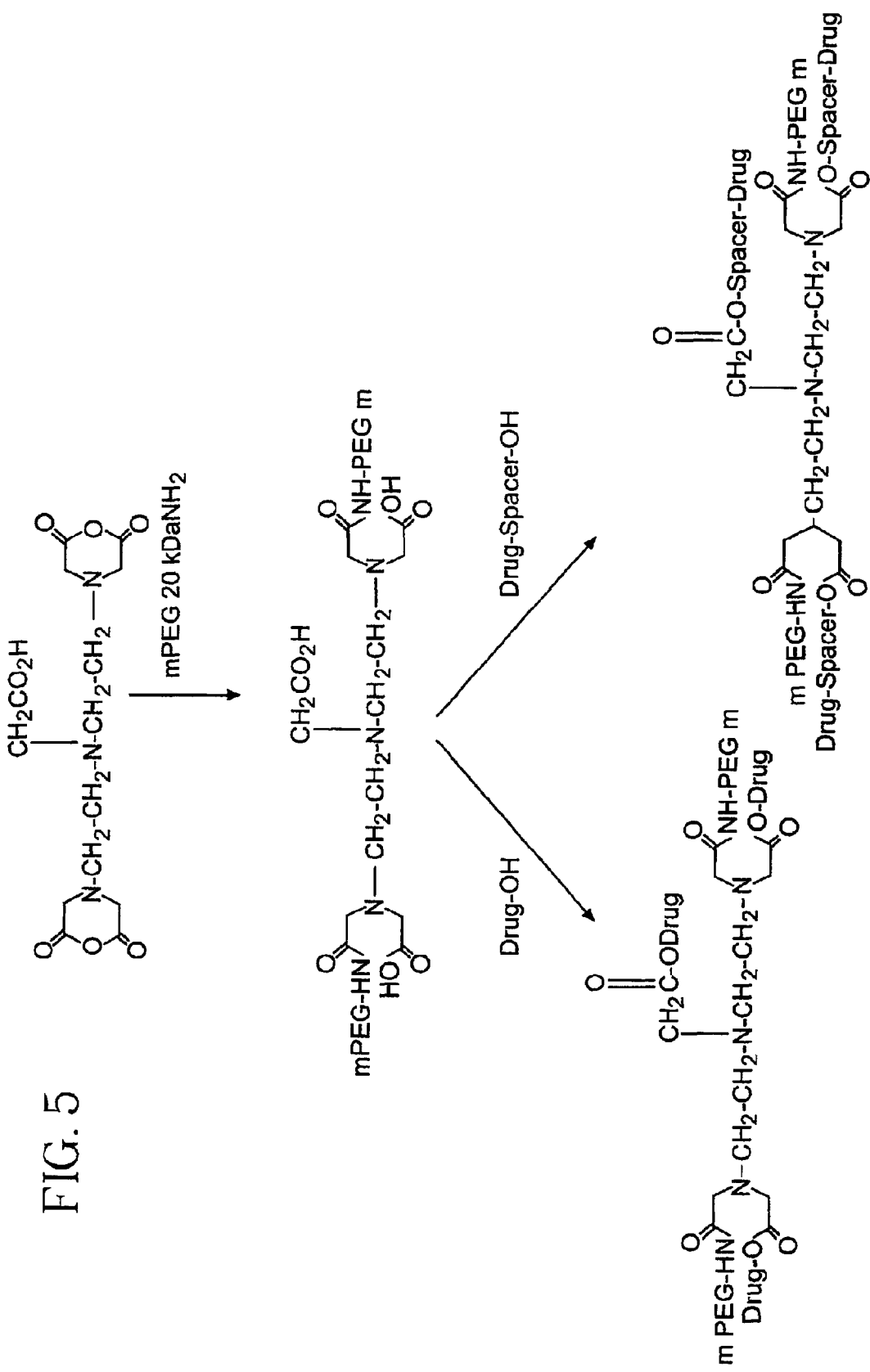
Figure 6:
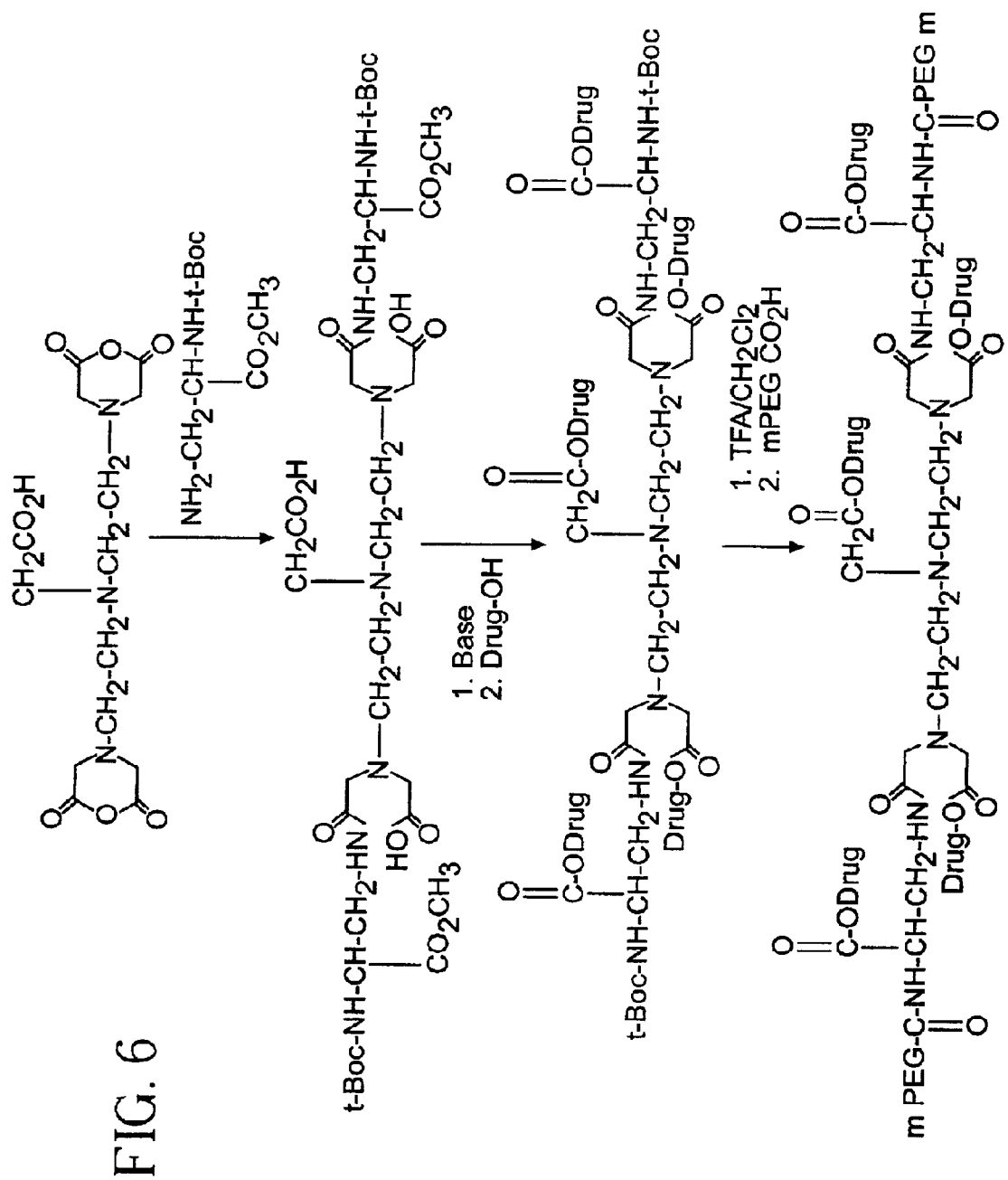
Figure 7:
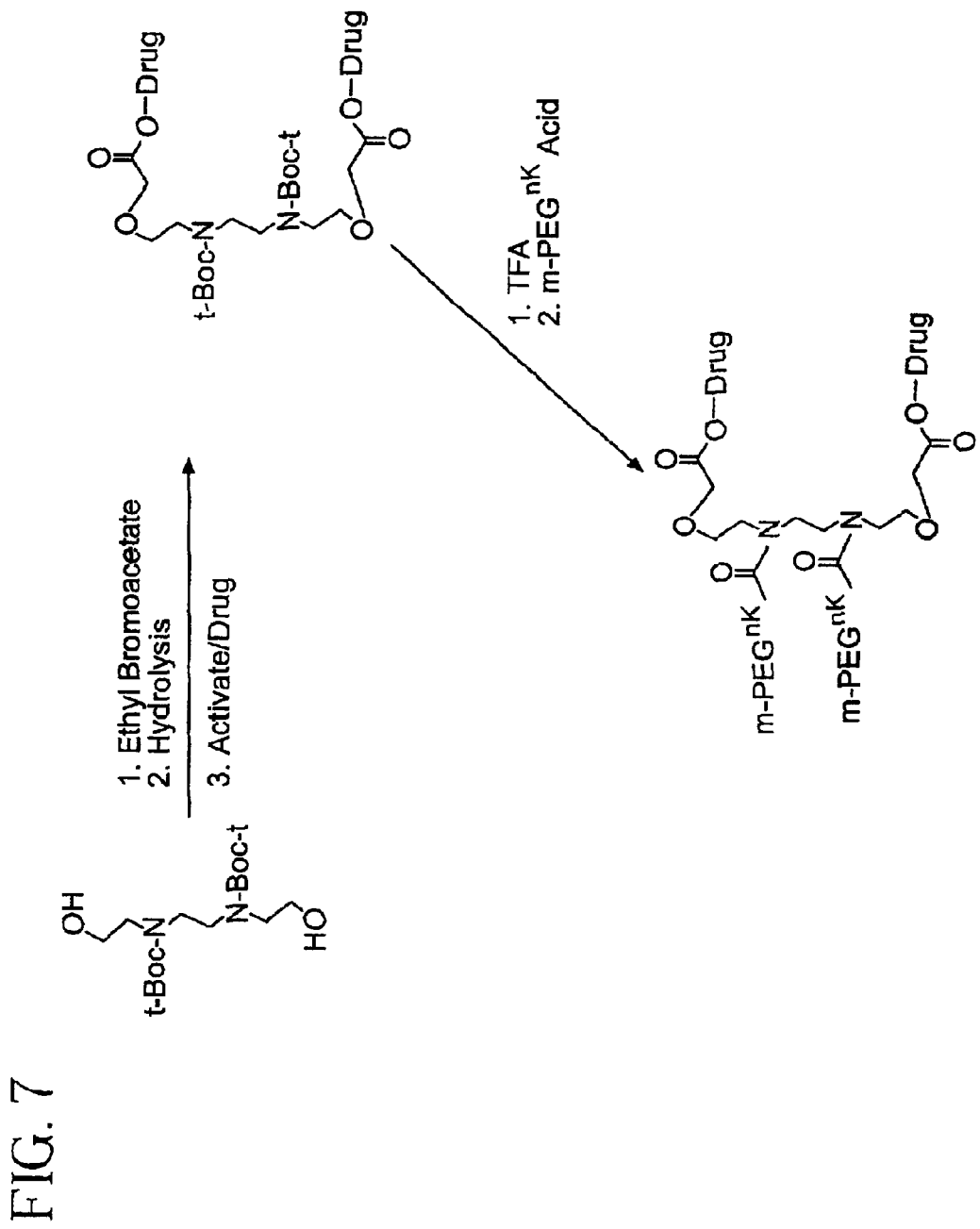
Figure 8:
Figure 9:
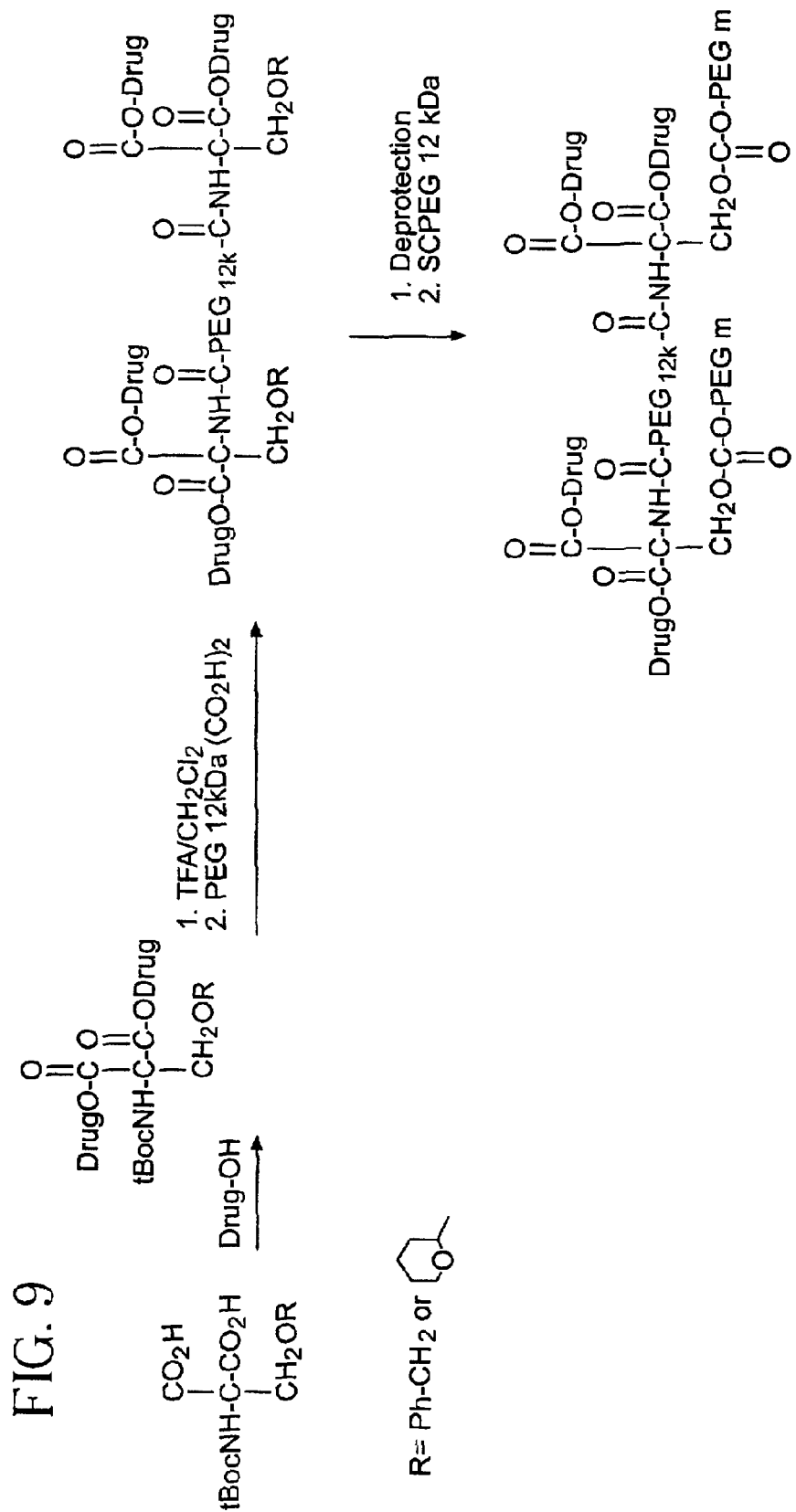
Figure 10:
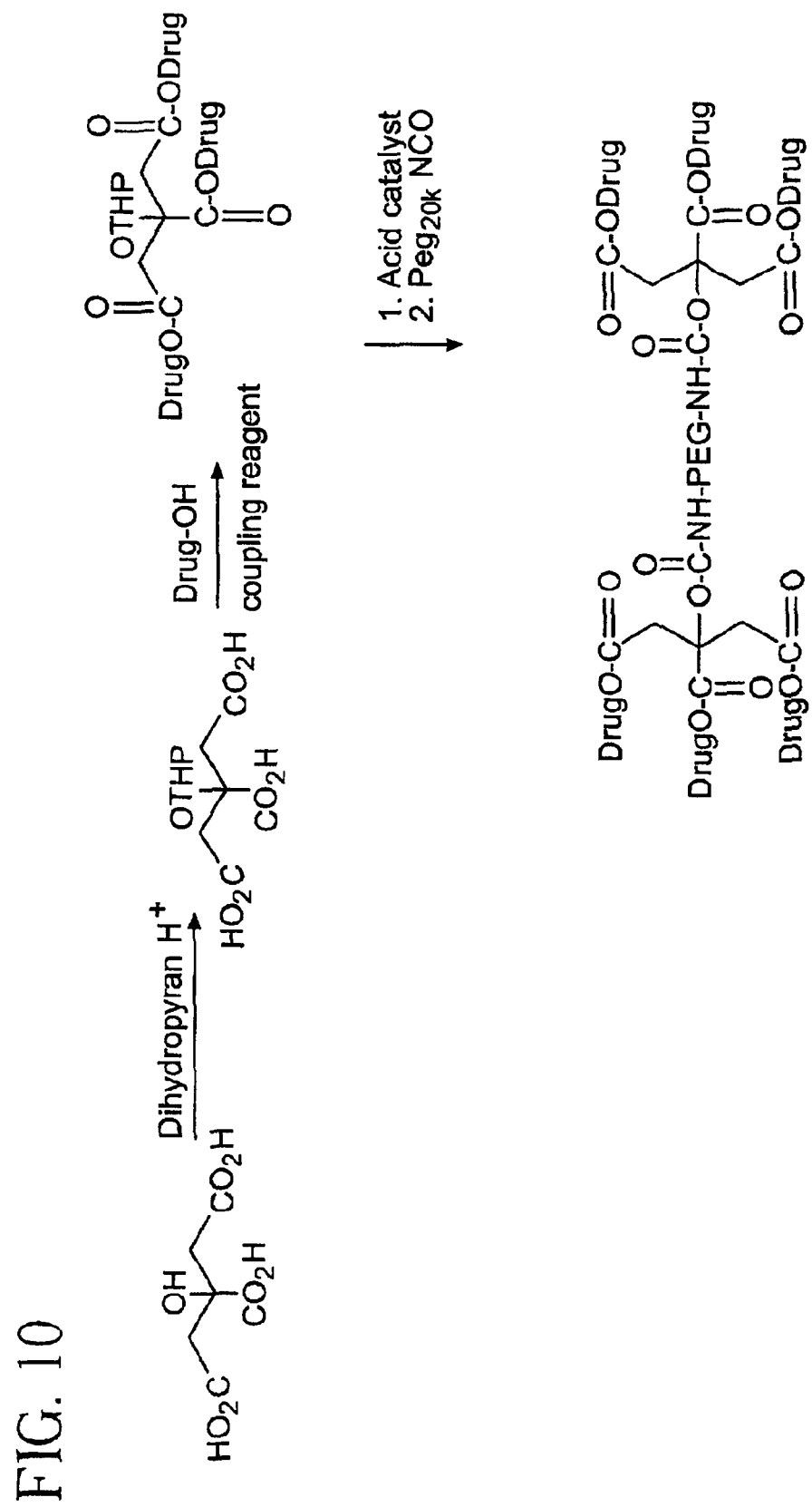
Figure 11:
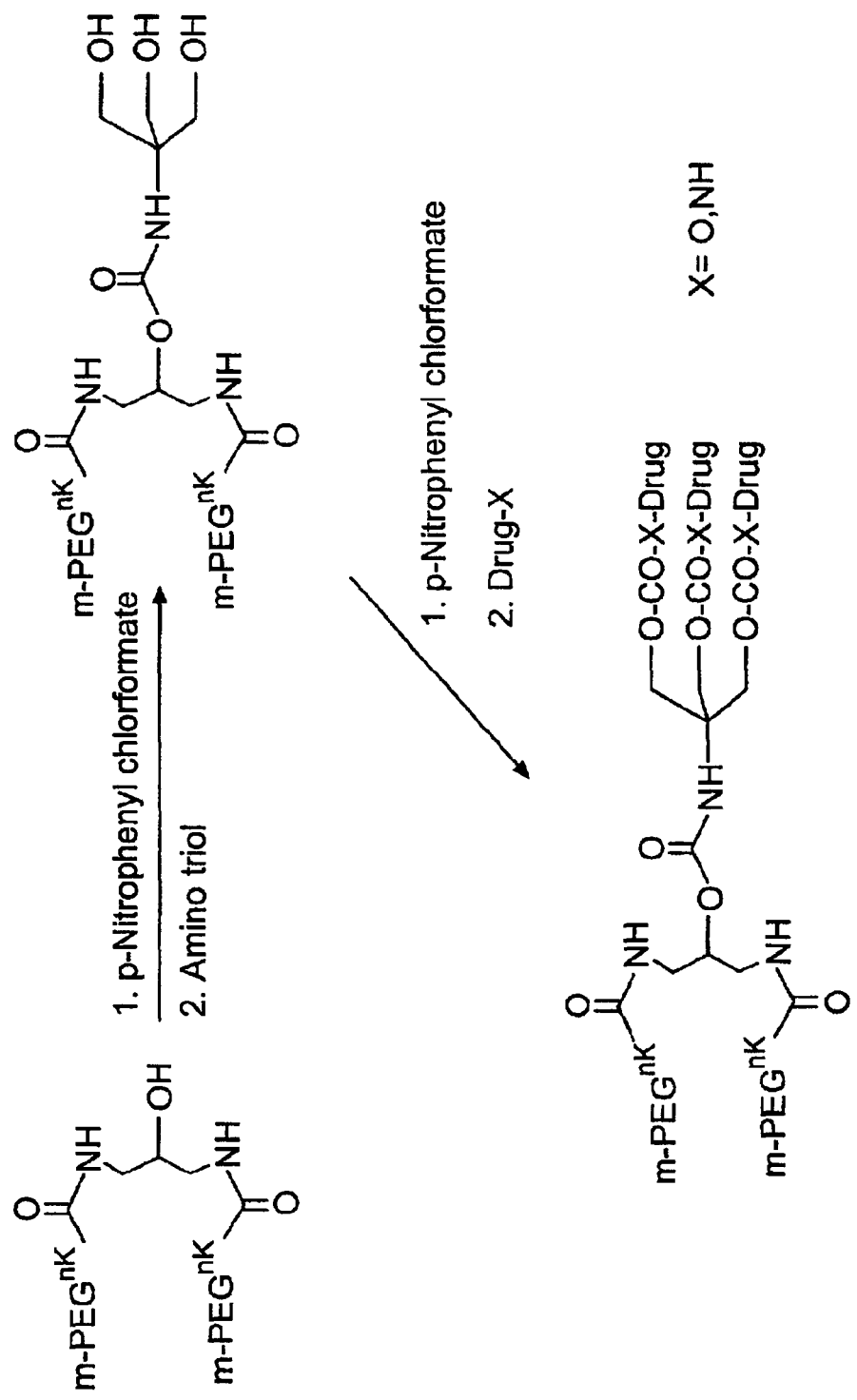

In additional aspects of the invention, such as those illustrated in FIGS. 4 and 5, a spacer is employed between the drug and the multifunctional moiety. Although schemes show the drug-spacer intermediate being reacted with the multifunctional moiety, those of ordinary skill will understand that the spacer can be attached to the multifunction prior to reacting with the drug target.

Attachment of the D moiety, e.g., Drug-OH or Drug-NH$_2$ is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphonic acid, cyclic anhydride (PPACA) and phenyl dichlorophosphates, etc. which are available, for example, from commercial sources such as Sigma-Aldrich Chemical, or synthesized using known techniques.

Preferably, the substituents are reacted in an inert solvent such as methylene chloride, chloroform, toluene, DMF or mixtures thereof. The reaction also preferably is conducted in the presence of a base, such as dimethylamino-pyridine, dlisopropylethylamine, pyridine, triethlamine, etc. to neutralize any acids generated and at a temperature from 0° C. up to about 22° C. (room temperature).

Turning now to those aspects of the invention related to Formulae(X) and (XI), additional details are provided below. In some preferred aspects of the invention, the final products corresponding to formula (X) are prepared by reacting a compound of formula (XII)

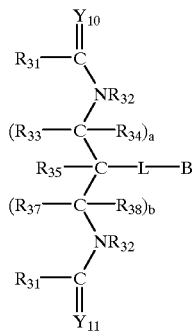

(XII)

wherein all variables are the same as that set forth above with regard to formula (X) and B is OH or a leaving group as described herein, such as an activated ester e.g., N-hydroxysuccinimidyl, benzotrialzole carbonate, N-hydroxyphthalimidyl, succinimidyl carbonate, para-nitrophenyl, thiazolidine thione, carbonyl diamidozole, with a compound of formula (XIII)

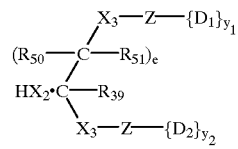

(XIII)

wherein all variables are the same as that set forth above with regard to formula (X), under conditions sufficient to cause a substitution reaction in which the compound of formula (X) is formed.

Figure 12A:
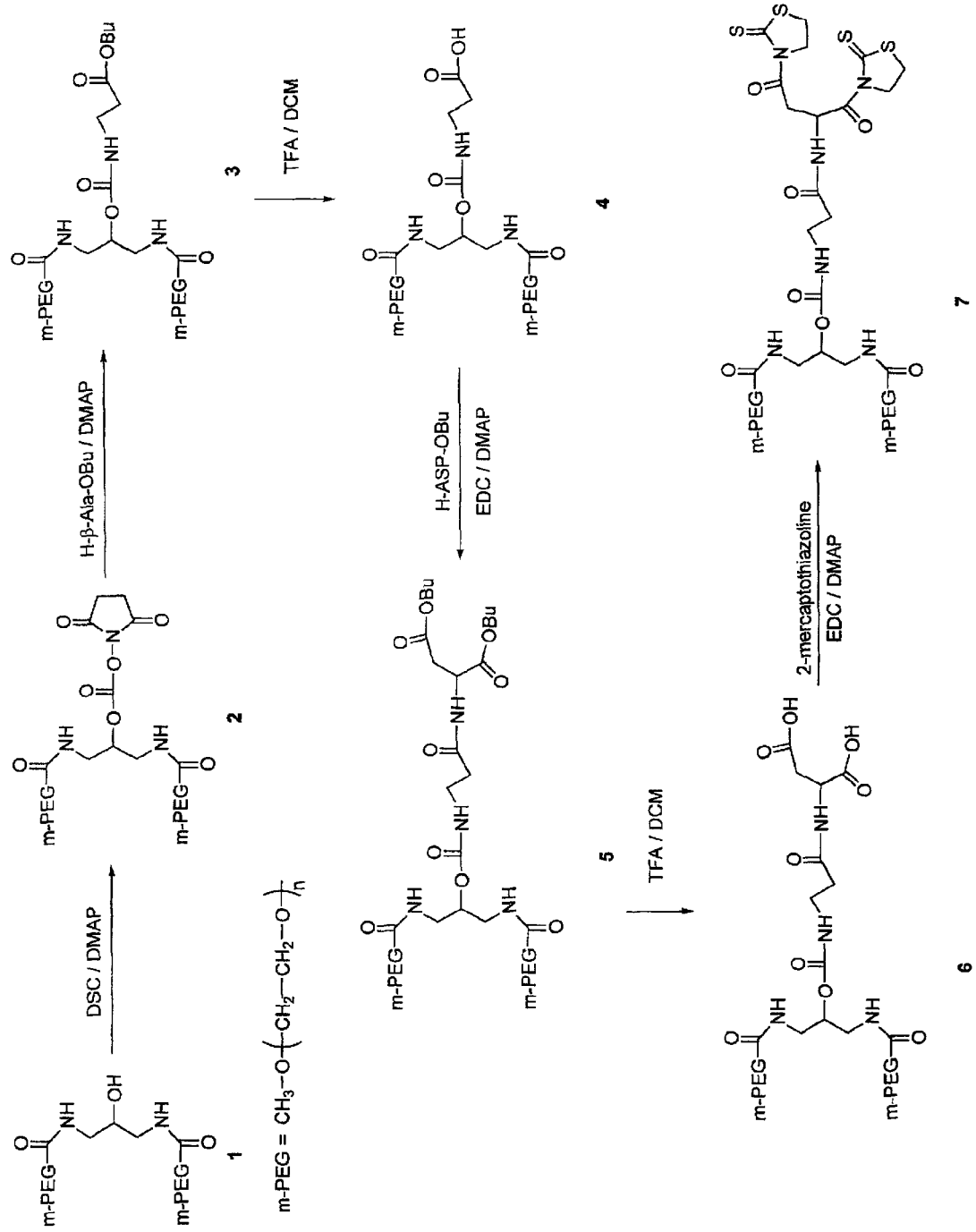
Figure 12B:
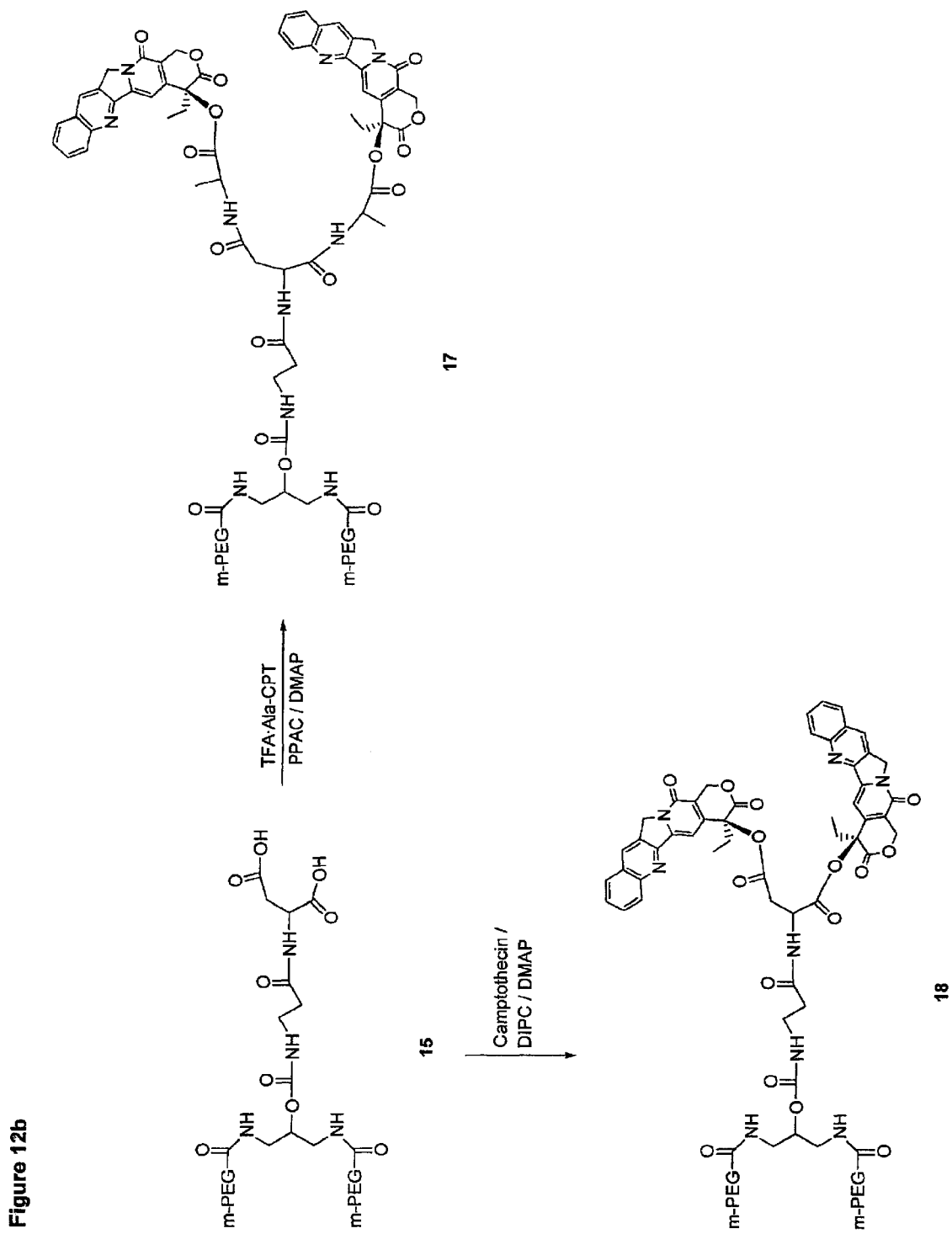
Figure 12C:
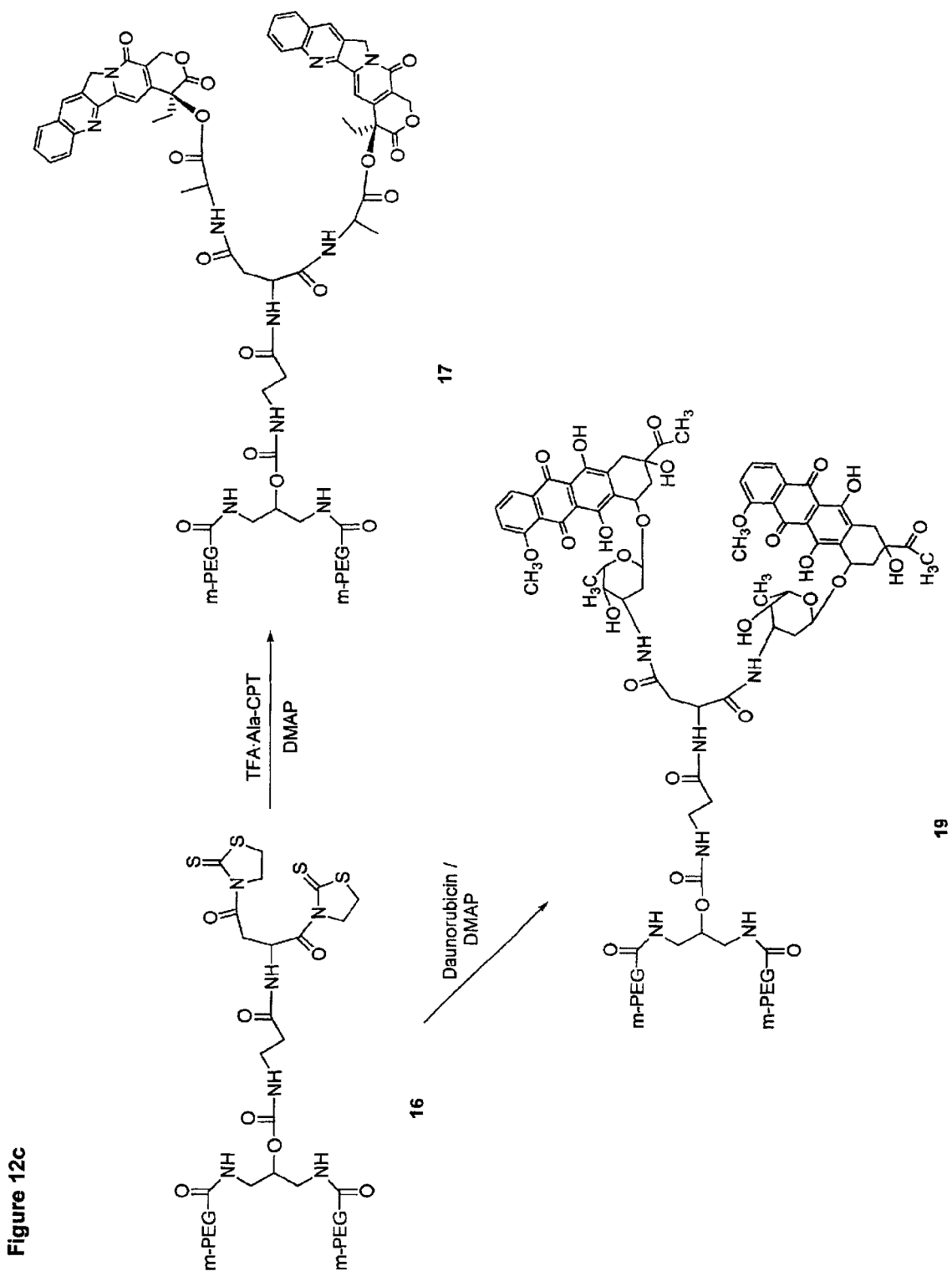
Figure 13:
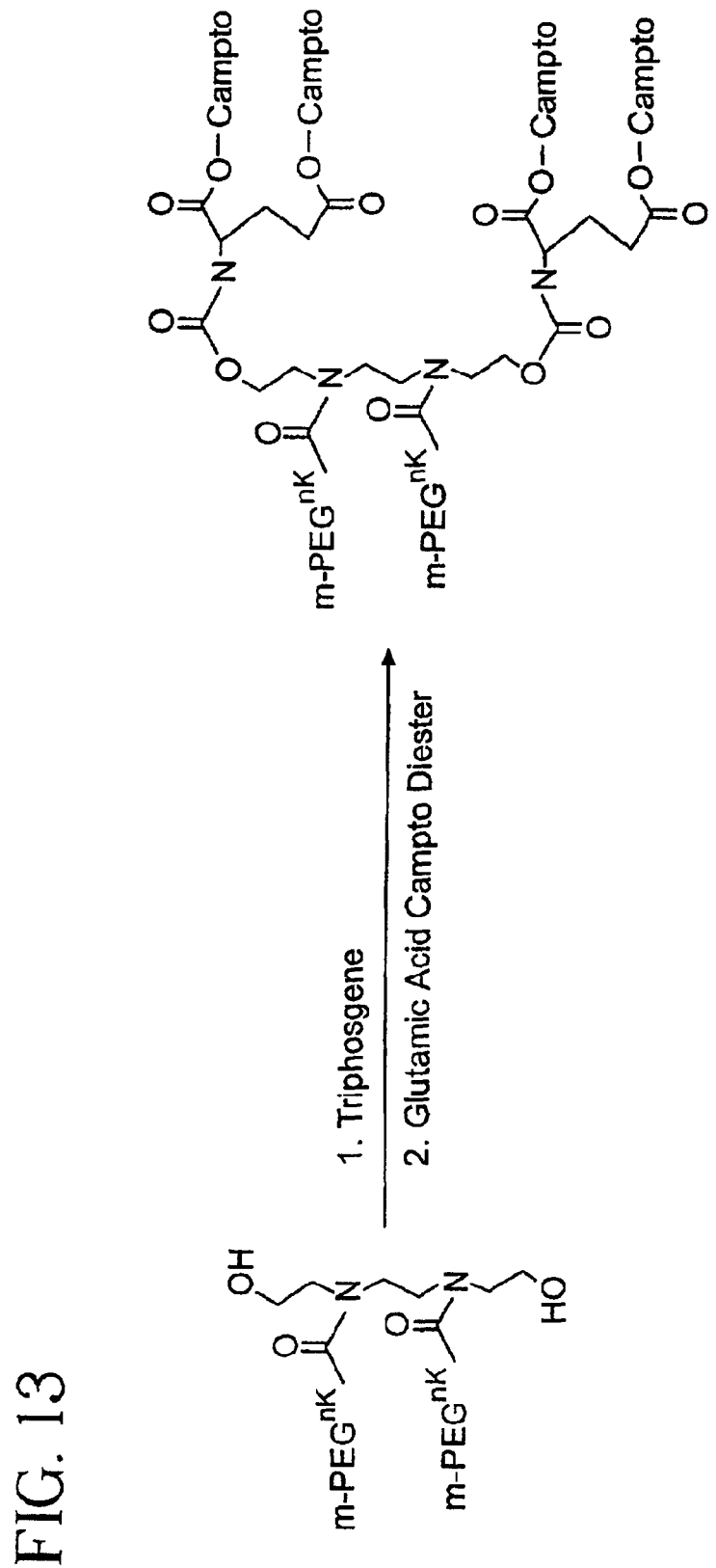
Figure 14:
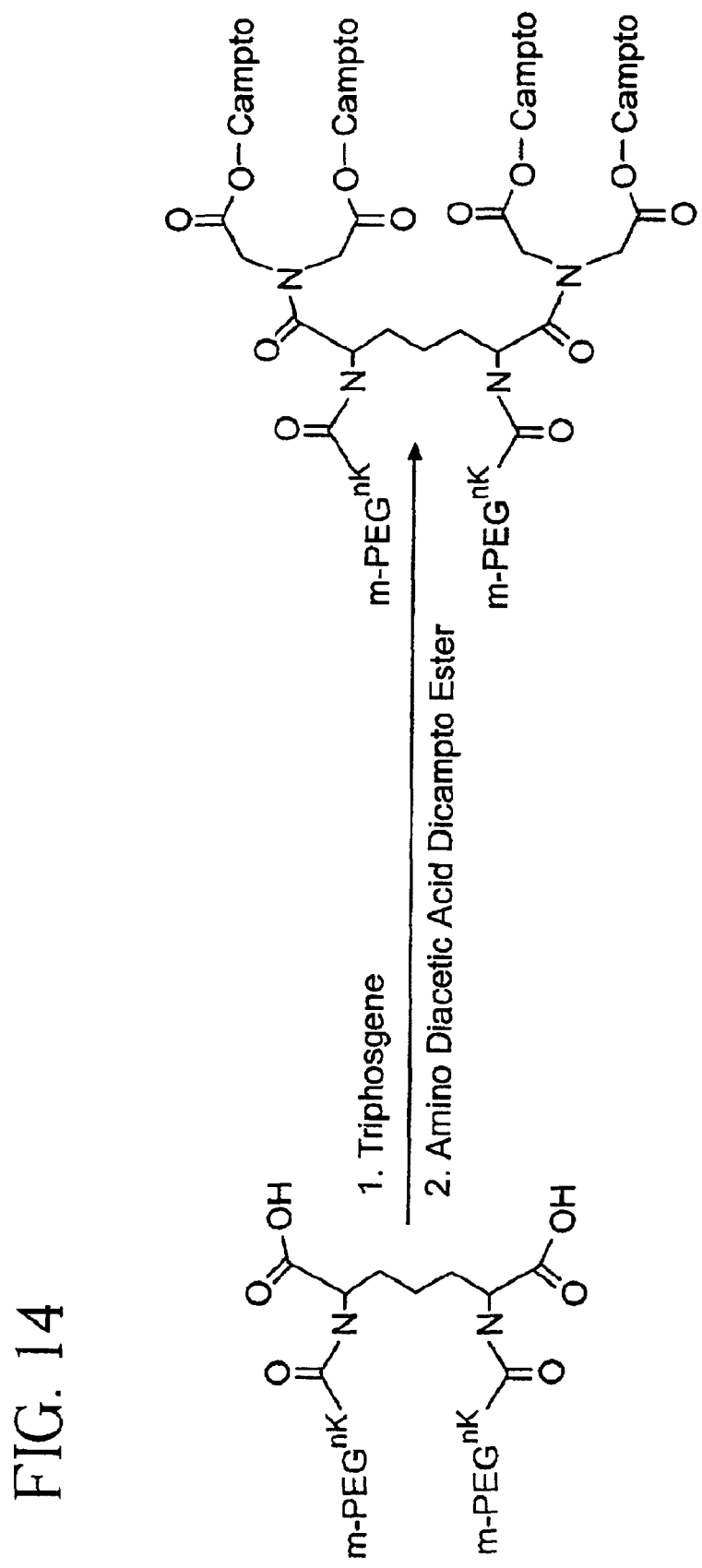
Figure 15:
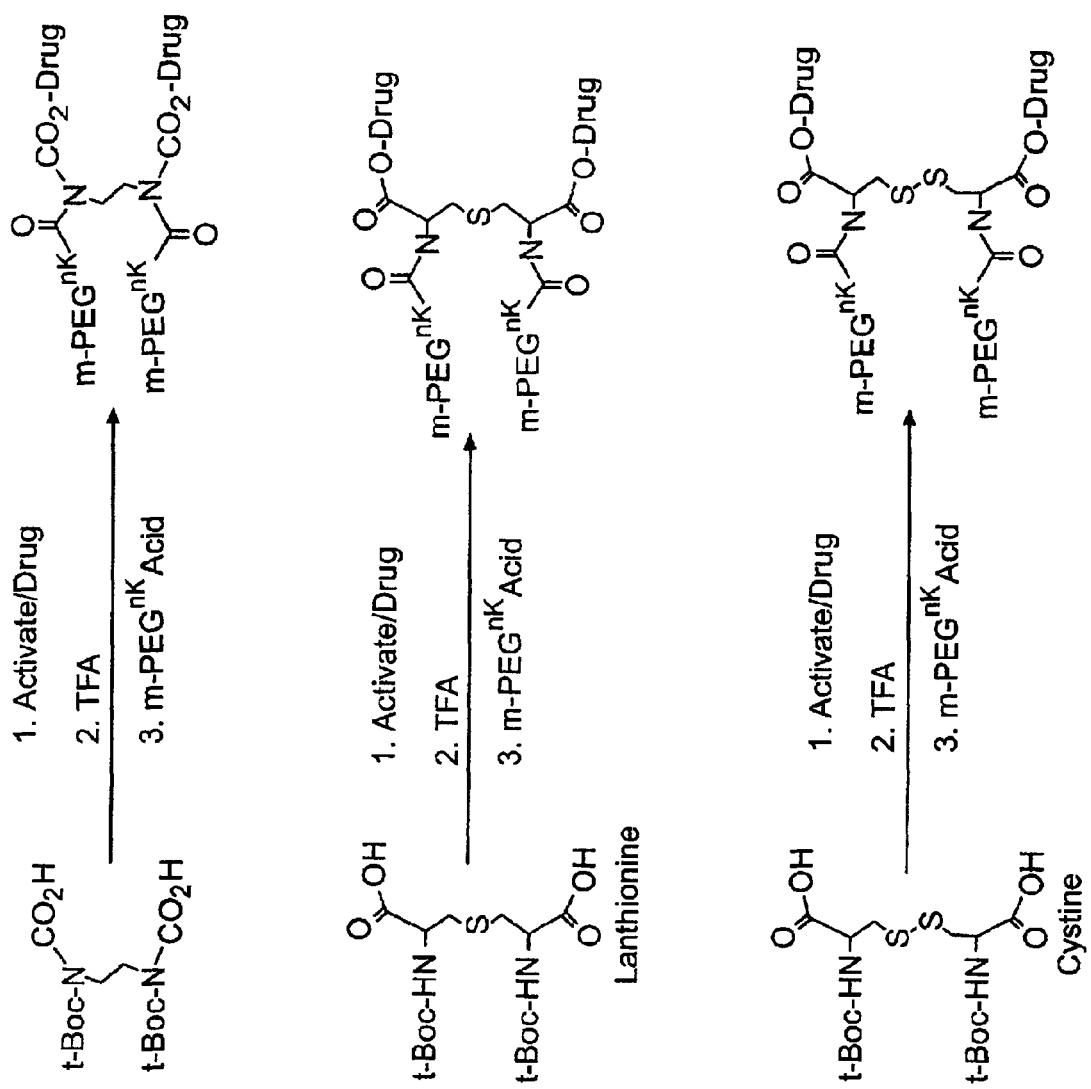
Figure 16:
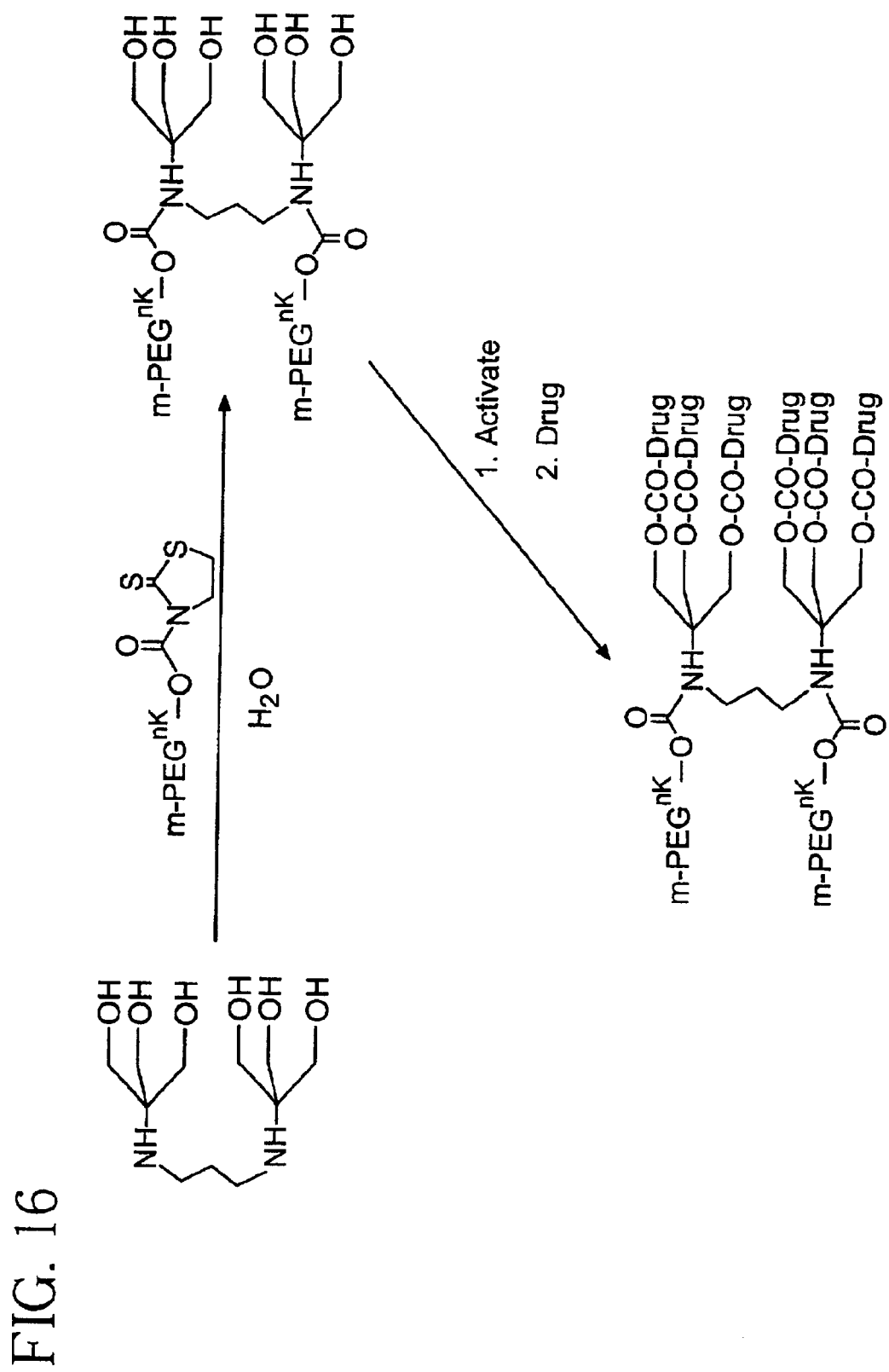
Figure 17:
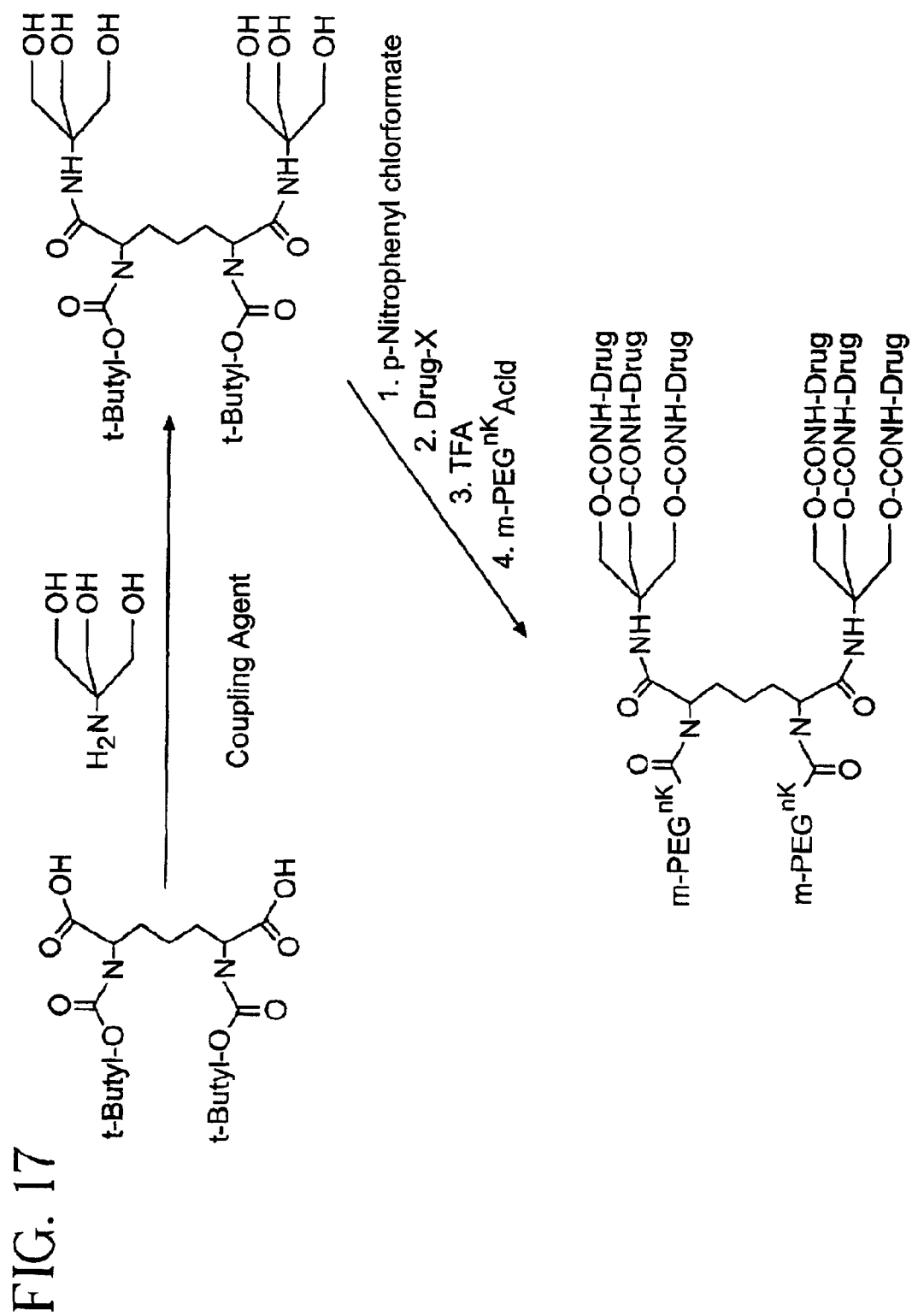

In an alternative aspect of the invention, the final product can be prepared by reacting a compound of formula (X) in which D$_1$ and D$_2$ are leaving groups or OH with a biologically active material containing an available OH or NH$_2$ group under conditions sufficient to cause the polymer-loaded final product to be formed, e.g with a coupling reagent such as DIPC, 1-[3-(dimethylamino) propyl]-3-ethylcarbodiimide hydrochloride (EDC), DCC, etc. and a base, if needed, like 4-dimethylaminopyridine (DMAP). See FIG. 12(b) and the examples corresponding thereto for the case where D$_1$ and D$_2$ are OH and FIG. 12(c) and the examples corresponding thereto where D$_1$ and D$_2$ are leaving groups for additional details related to these synthetic routines.

Additional details concerning synthetic techniques can be found in the Examples and in the Figures.

E. Methods of Treatment

Another aspect of the present invention provides methods of treatment for various medical conditions in mammals. The methods include administering to the mammal in need of such treatment, an effective amount of a prodrug, such as a camptothecin-20-PEG ester, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxanes are administered in amounts ranging from about 5 to about 500 mg/m$^2$ per day, based on the amount of the taxane moiety. Camptothecin prodrugs are also administered in amounts ranging from about 5 to about 500 mg/m$^2$ per day. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof

F. EXAMPLES

The following examples serve to provide further appreciation of the invention but are not meant in any way to restrict the effective scope of the invention. The underlined and bold-faced numbers recited in the Examples correspond to those shown in the Figures.

Example 1 t-Boc Aspartic Camptothecin (5)

A solution of 1.34 g (5.8 mmoles) of t-boc aspartic acid, 2.0 g (5.8 mmoles) of camptothecin and 0.7 g (5.8 mmoles) of n-dimethylamino pyridine in 25 ml of dry dichloromethane was cooled to 0° C. followed by the addition of 0.72 g (5.8 mmoles) of diisopropylcarbodiimide. This mixture was allowed to warm to room temperature overnight followed by washing with 1% aqueous sodium bicarbonate and 0.1 N HCl solution. The organic layer was dried over anhydrous sodium sulfate, and the solvent was removed by distillation in vacuo. The residue was crystallized from methanol to yield 2.1 g (40% yield) of product.

C$^{13}$NMR assignments: 7.47, 28.12, 31.48, 35.66, 49.74, 66.83, 80.11, 96.25, 119.64, 127.79, 127.91, 128.17, 128.36, 129.48, 130.40, 130.92, 145.20, 146.05, 148.59, 152.07, 155.18, 156.84, 166.51, 167.22, and 169.90 ppm

Example 2

Aspartic Camptothecin, TFA Salt (6)

A solution of 0.5 g (0.56 mmoles) of t-boc aspartic camptothecin in 2.5 ml of trifluoroacetic acid and 5.0 ml of dichloromethane was stirred at room temperature for one hour, followed by the addition of 40 ml of ethyl ether. The solid was collected by filtration, washed with ethyl ether and dried to yield 0.4 g (75% yield) of product. This material was used without further purification.

Example 3 t-Boc Diaminopimelic Acid (1)

A solution of 3.0 g (16 mmoles) of 2,6-diaminopimelic acid and 7.5 g (34 mmoles) of di-t-butyldicarbonate in 50 ml of dioxane, 25 ml of water and 25 ml of 1 N NaOH was stirred overnight at room temperature. The dioxane was removed from the reaction mixture by distillation in vacuo, the aqueous residue was adjusted to pH 3.5 with hydrochloric acid, and extracted with dichloromethane to yield 3.0 g (48% yield) of product.

C$^{13}$NMR assignments: 27.42, 28.20, 30.45, 54.17, 81.91, 160.23, and 175.90 ppm.

Example 4 t-Boc Diaminopimelic Aspartic Camptothecin (7)

A solution of 41 mg (0.11 mmoles) of t-boc diaminopimelic acid, 220 mg (0.23 mmoles) of aspartic camptothecin TFA salt, 0.14 ml (0.21 mmoles) of a 50% solution of 1-propanephosphonic acid cyclic anhydride in ethyl acetate and 54 mg (0.44 mmoles) of N-dimethylamino pyridine in 20 ml of dry dichloromethane was stirred at room temperature overnight followed by washing with 1% aqueous sodium bicarbonate and 0.1 N HCl solution. The organic layer was dried over anhydrous sodium sulfate, and the solvent was removed by distillation in vacuo. The residue was crystallized from methanol to yield 180 mg (81% yield) of product.

Example 5

Diaminopimelic Aspartic Camptothecin TFA Salt (8)

A solution of 61 mg (0.030 mmoles) of t-boc diaminopimelic aspartic camptothecin in 2.5 ml of trifluoroacetic acid and 5.0 ml of dichloromethane was stirred at room temperature for one hour, followed by the addition of 40 ml of ethyl ether. The solid was collected by filtration, washed with ethyl ether and dried to yield 61 mg (98% yield) of product.

Example 6 m-PEG$^{20K}$ Diaminopimelic Aspartic Camptothecin (9)

A solution of 1.1 g (0.05 mmoles) of m-PEG$^{20k}$ acid, 61 mg (0.03 mmoles) of diaminopimelic aspartic acid camptothecin TFA salt, 0.032 ml (0.05 mmoles) of a 50% solution of 1-propanephosphonic acid cyclic anhydride in ethyl acetate and 12 mg (0.10 mmoles) of N-dimethylamino pyridine in 20 ml of dry dichloromethane was stirred at room temperature overnight followed by washing with 1% aqueous sodium bicarbonate and 0.1 N HCl solution. The organic layer was dried over anhydrous sodium sulfate, and the solvent was removed by distillation in vacuo. The residue was crystallized from 2-propanol to yield 0.8 g (80% yield) of product. Camptothecin fragments by UV analysis: 3.6

Example 7 t-Boc Diaminopimelic Camptothecin (2)

A solution of 0.5 g (1.3 mmoles) of t-boc diaminopimelic acid, 0.7 g (2.0 mmoles) of camptothecin, 0.4 ml (2.6 mmoles) of a 50% solution of 1-propane phosphonic acid cyclic anhydride in ethyl acetate and 0.3 g (2.5 mmoles) of N-dimethylamino pyridine in 20 ml of dry dichloromethane was stirred at room temperature overnight followed by washing with 1% aqueous sodium bicarbonate and 0.1 N HCl solution. The organic layer was dried over anhydrous sodium sulfate, and the solvent was removed by distillation in vacuo. The residue was crystallized from methanol to yield 1.1 g (81% yield) of product.

$C^{13}$NMR assignments: 7.56, 25.30, 28.06, 28.38, 31.59, 49.87, 53.01, 64.29, 66.91, 79.82, 96.82, 119.47, 127.81, 127.94, 128.30, 129.89, 130.42, 130.87, 146.22, 148.53, 152.27, 155.62, 157.29, 167.12, and 171.43 ppm

Example 8

Diaminopimelic Camptothecin TFA Salt (3)

A solution of 0.75 g (0.71 mmoles) of t-boc diaminopimelic camptothecin in 4.0 ml of trifluoroacetic acid and 8.0 ml of dichloromethane was stirred at room temperature for one hour, followed by the addition of 50 ml of ethyl ether. The solid was collected by filtration, washed with ethyl ether and dried to yield 0.75 (97% yield) of product.

Example 9 m-PEG$^{20K}$ Diaminopimelic Camptothecin (4)

A solution of 2.0 g (0.10 mmoles) of m-PEG$^{20k}$ acid, 60 mg (0.06 mmoles) of diaminopimelic camptothecin TFA salt, 0.064 ml (0.10 mmoles) of a 50% solution of 1-propanephosphonic acid cyclic anhydride in ethyl acetate and 25 mg (0.20 mmoles) of N-dimethylamino pyridine in 20 ml of dry dichloromethane was stirred at room temperature overnight followed by washing with 1% aqueous sodium bicarbonate and 0.1 N HCl solution. The organic layer was dried over anhydrous sodium sulfate, and the solvent was removed by distillation in vacuo. The residue was crystallized from 2-propanol to yield 1.85 g (93% yield) of product.

Camptothecin fragments by UV analysis: 1.6

Example 10

A solution of 10 (10.0 g, 4.14 mmol), 4-dimethylaminopyridine (DMAP, 1.01 g, 8.28 mmol), and N,N'-disuccinimidyl carbonate (DSC, 2.12 g, 8.28 mmol) in 100 ml of dry methylene chloride was stirred for 18 hours at room temperature. The solvent was partially removed from the reaction mixture by rotary evaporation, followed by precipitation with ethyl ether. The solid was collected by filtration, washed with ether and crystallized from methylene chloride/ethyl ether to yield 11 (9.0 g, 3.73 mmol, 90%). The structure was confirmed by $^{13}$C NMR.

Example 11

A solution of 11 (7.0 g, 0.29 mmol), β-alanine t-butyl ester hydrochloride (0.21 g, 1.15 mmol), and diisopropylethyl amine (0.22 g, 1.73 mmol) in 60 ml of dry methylene chloride was stirred for 18 hours at room temperature. The solvent was partially removed from the reaction mixture under reduced pressure, followed by precipitation with ethyl ether. The solid was collected by filtration, washed with ether and crystallized from 2-propanol to yield 12 (6.6 g, 0.27 mmol, 94%). The structure was confirmed by $^{13}$C NMR (67.8 MHz, CDCl$_3$) with peaks at: δ 27.6, 34.9, 36.2, 40.7, 58.5, 63.5, 69.0–71.4 (PEG), 80.3, 155.1, 156.3, and 170.8.

Example 12

A solution of 12 (6.3 g, 0.27 mmol) in 70 ml of methylene chloride and 35 ml of trifluoro acetic acid was stirred for 2 hours at room temperature, followed by removal of the methylene chloride by rotary evaporation. The product was precipitated from the trifluoro acetic acid with ethyl ether, washed with ether, and crystallized from 2-propanol to yield 13 (5.4 g, 0.23 mmol, 86%). The structure was confirmed by $^{13}$C NMR (67.8 MHz, CDCl3) with peaks at: δ 22.5, 33.6, 36.3, 40.8, 58.6, 63.6, 68.4–72.1 (PEG), 155.3, 156.4, and 172.7.

Example 13

A solution of 13 (5.2 g, 0.21 mmol), aspartic acid t-butyl ester hydrochloride (0.2 g, 0.71 mmol), and DMAP (0.14 g, 1.15 mmol) in 50 ml of dry methylene chloride was cooled to 0° C., followed by addition of 1-[3-(dimethylamino) propyl]-3-ethylcarbodiimide hydrochloride (EDC, 0.082 g, 0.43 mmol). This mixture was allowed to warm to room temperature overnight, followed by partial removal of the solvent under reduced pressure and precipitation with ethyl ether. The solid was collected by filtration, washed with ether and crystallized from 2-propanol to yield 14 (4.7 g, 0.19 mmol, 90%). The structure was confirmed by $^{13}$C NMR (67.8 MHz, CDCl$_3$) with peaks at: δ 27.5, 27.6, 35.4, 36.9, 41.0, 48.7, 58.6, 63.6, 68.4–72.1, 81.1, 82.0, 155.3, 156.4, 169.6, 169.9, and 170.8.

Example 14

A solution of 14 (4.4 g, 0.18 mmol) in 50 ml of methylene chloride and 25 ml of trifluoroacetic acid was stirred for 2 hours at room temperature, followed by removal of the methylene chloride by rotary evaporation. The product was precipitated from the trifluoro acetic acid with ethyl ether, washed with ether, and crystallized from 2-propanol to yield 15 (4.1 g, 0.17 mmol, 93%). The structure was confirmed by $^{13}$C NMR.

Example 15

A solution of 15 (4.0 g, 0.16 mmol), 2-mercaptothiazoline (0.076 g, 0.64 mmol), and DMAP (0.078 g, 0.64 mmol) in 40 mL dry methylene chloride is cooled to 0° C., followed by addition of EDC (0.12 g, 0.64 mmol). This mixture is allowed to warm to room temperature overnight, followed by partial removal of the solvent concentration of the solvent under reduced pressure and precipitation with ethyl ether. The solid is collected by filtration, washed with ether and crystallized from methylene chloride/ethyl ether to yield 16 (3.6 g, 0.144 mmol, 90%). The structure is confirmed by $^{13}$C NMR.

Example 16

To a solution of 15 (1.2 g, 0.050 mmol), camptothecin alaninate TTA salt (0.11 g, 0.20 mmol), and DMAP (0.048 g, 0.40 mmol) in 20 ml of methylene chloride is added 1-propanephosphonic acid cyclic anhydride (0.070 g, 0.22 mmol). This mixture is stirred to room temperature overnight, followed by partial removal of the solvent by rotary evaporation and precipitation with ethyl ether. The solid was collected by filtration, washed with ether and crystallized from 2-propanol to yield 17 (1.1 g, 0.045 mmol, 90%). The structure is confirmed by $^{13}$C NMR.

Example 17

To a solution of 16 (1.2 g, 0.050 mmol) and DMAP (0.024 g, 0.20 mmol) in 20 ml of methylene chloride is added camptothecin alaninate TFA salt (0.11 g, 0.20 mmol). This mixture is stirred at room temperature overnight, followed by partial removal of the solvent under reduced pressure and precipitation with ethyl ether. The solid is collected by filtration, washed with ether and crystallized from 2-propanol to yield 17 (1.1 g, 0.045 mmol, 90%). The structure is confirmed by $^{13}$C NMR.

Example 18

A solution of 15 (1.2 g, 0.050 mmol), camptothecin (0.70 g, 0.20 mmol), and DMAP (0.024 g, 0.20 mmol) in 20 ml of methylene chloride is cooled to 0° C., followed by addition of 1,3-diisopropylcarbodiimide (0.025 g, 0.20 mmol). This mixture is allowed to warm to room temperature overnight, followed by partial removal of the solvent by rotary evaporation and precipitation with ethyl ether. The solid is collected by filtration, washed with ether and recrystallized from 2-propanol to yield 18 (1.1 g, 0.045 mmol, 90%). The structure is confirmed by $^{13}$C NMR.

Example 19

To a solution of 16 (1.2 g, 0.050 mmol) and DMAP (0.024 g, 0.20 mmol) in 20 ml of methylene chloride is added Daunorubicin hydrochloride salt (0.11 g, 0.20 mmol). This mixture is stirred at room temperature overnight, followed by partial removal of the solvent under reduced pressure and precipitation with ethyl ether. The solid is collected by filtration, washed with ether and crystallized from 2-propanol to yield 19 (1.1 g, 0.029 mmol, 90%). The structure is confirmed by $^{13}$C NMR.

We claim:

1. A compound of the formula:

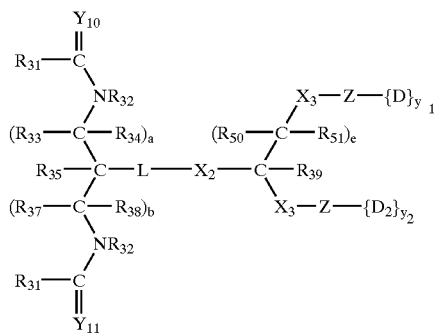 (X)

wherein:

$R_{31}$ is a linear or branched polymer residue;

$Y_{10}$ and $Y_{11}$ are independently O, S, or $NR_{40}$;

$X_2$ is O, S or $NR_{41}$;

$R_{32}, R_{33}, R_{34}, R_{35}, R_{37}, R_{38}, R_{39}, R_{40}, R_{41}, R_{50}$ and $R_{51}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls, a, b and e are each independently a positive integer.

L is an amino acid residue or a bifunctional linker;

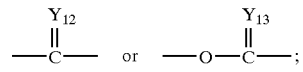

wherein $Y_{12}$ and $Y_{13}$ are independently O, S, or $NR_{41}$;

Z is selected from the group consisting of a bond, a moiety that is actively transported into a target cell, a hydrophobic moiety, and combinations thereof;

$D_1$ and $D_2$ are independently selected from the group consisting of OH, a residue of a hydroxyl-containing moiety, a residue of an amine-containing moiety and a leaving group; and $Y_1$ and $Y_2$ are independently selected positive integers.

2. The compound of claim 1, wherein $R_1$ is $O-(CH_2CH_2O)_x$ or $O-(CH(CH_3)CH_2O)_x$, wherein x is from about 10 to about 2,300.

3. The compound of claim 1 wherein L is selected from the group consisting of:

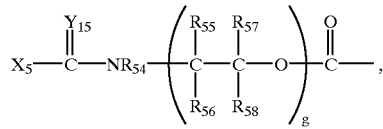

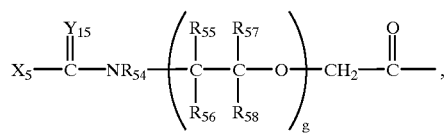

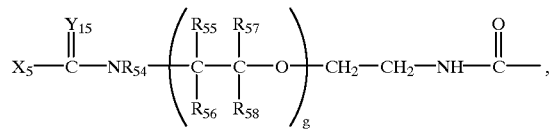

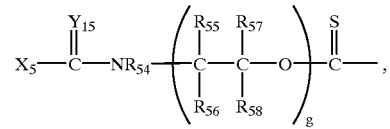

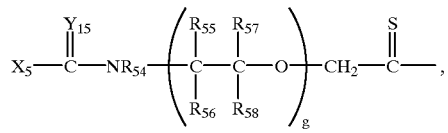

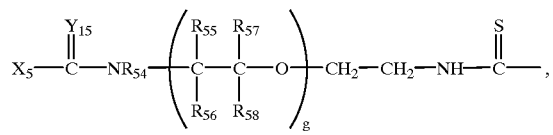

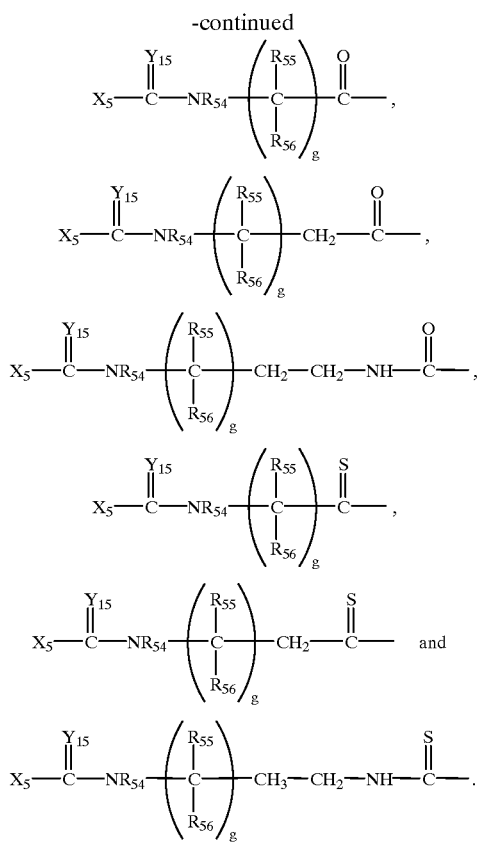

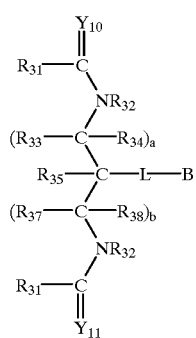

wherein $X_5$ is O, S, or N $R_{43}$;

$Y_{15}$ is O, S, or $NR_{44}$;

$R_{43}$, $R_{44}$ and $R_{54}$–$R_{58}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls; and g is a positive integer.

4. The compound of claim 1 wherein $D_1$ and $D_2$ are residue of an active biological agent, an anticancer prodrug, a detectable tag, and combinations thereof.

5. A method of preparing a polymeric conjugate, comprising reacting a compound of formula (XII)

(XII)

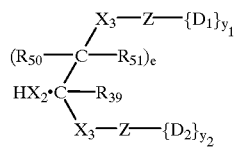

wherein $R_{31}$ is a linear or branched polymer residue;

$Y_{10}$ and $Y_{11}$ are independently O, S, or $NR_{40}$;

L is an amino acid residue or a bifunctional linker;

$R_{32}$, $R_{33}$, $R_{34}$, $R_{35}$, $R_{37}$, $R_{38}$, and $R_{40}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

a and b are each independently a positive integer, and

B is a leaving group;

with a compound of the formula (XIII)

(XIII)

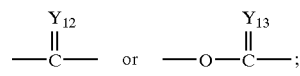

wherein $X_2$ is O, S, or $NR_{41}$;

$R_{39}$, $R_{41}$, $R_{50}$ and $R_{51}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls and substituted $C_{1-6}$ heteroalkyls;

$$\underset{C}{\overset{Y_{12}}{\overset{\|}{-}}}- \quad \text{or} \quad -O-\underset{C}{\overset{Y_{13}}{\overset{\|}{-}}}-;$$

wherein $Y_{12}$ and $Y_{13}$ are independently O, S, or $NR_{41}$;

Z is selected from the group consisting of a bond, a moiety that is actively transported into a target cell, a hydrophobic moiety, and combinations thereof;

$D_1$ and $D_2$ are independently selected from the group consisting of OH, a residue of a hydroxyl, a residue of an amine-containing moiety and a leaving group;

e is a positive integer; and $y_1$ and $y_2$ are independently selected positive integers;

under conditions sufficient to cause a substitution reaction in which the compound of formula (X) is formed, and isolating the polymer conjugate of formula (X).

6. A method of treating mammals with polymeric conjugates, comprising administering an effective amount of the compound of claim 1.

7. The compound of claim 3 wherein g is 1 or 2.

8. The compound of claim 2, wherein $R_{31}$ is a polymer having a weight average molecular weight ranging from about 2,000 to about 100,000.

9. The compound of claim 2, wherein $R_{31}$ is a polymer having a weight average molecular weight of from about 5,000 to about 50,000.

10. The compound of claim 2, wherein $R_{31}$ is a polymer having a weight average molecular weight of from about 20,000 to about 40,000.

11. The compound of claim 1, having the formula:

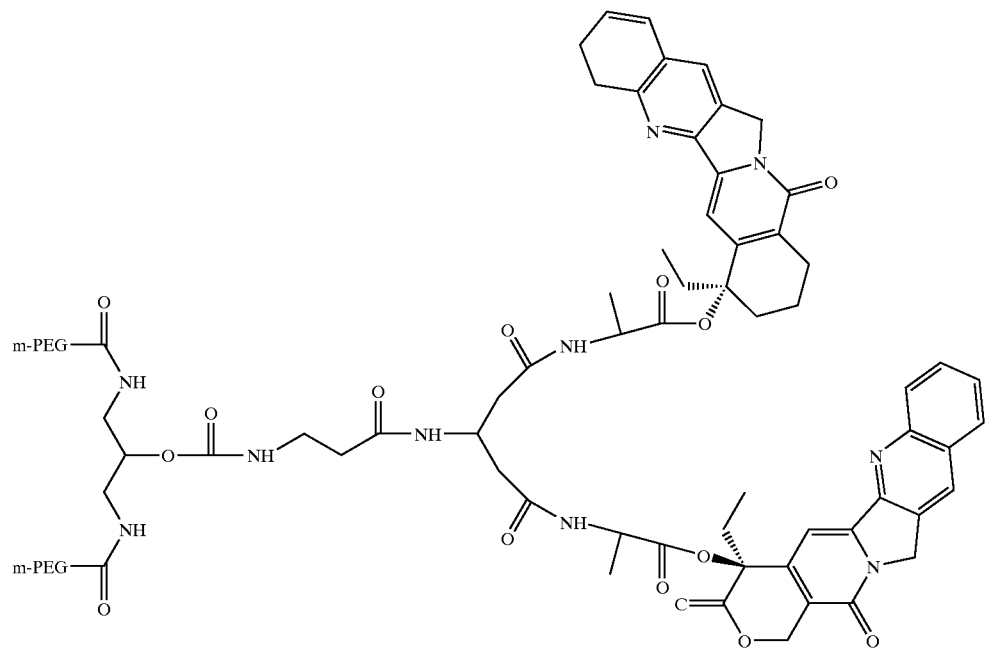
12. The compound of claim 1, wherein $Y_{11}$ and $Y_{12}$ are both.
13. The compound of claim 1, wherein $R_{32}$–$R_{35}$, $R_{37}$–$R_{40}$, $R_{50}$, and $R_{51}$ are each hydrogen.
14. The compound of claim 1, wherein a and b are each 1.
15. The compound of claim 1, wherein $y_1$ and $y_2$ are both or 1.
* * * * *